US012678279B2

(12) United States Patent
Wong et al.

(10) Patent No.: US 12,678,279 B2
(45) Date of Patent: Jul. 14, 2026

(54) SYSTEMS AND METHODS FOR DEPLOYING AND RETRIEVING A PROSTHESIS

(71) Applicant: NEOVASC INC., Toronto (CA)

(72) Inventors: Karen Tsoek-Ji Wong, Richmond (CA); Kellen Bodell, Plymouth, MN (US); Aaron J. Chalekian, Savage, MN (US); Eric Soun-Sang Fung, Vancouver (CA); Kathleen Hung, New Westminster (CA)

(73) Assignee: NEOVASC INC., Ontario (CA)

( * ) Notice: Subject to any disclaimer, the term of this patent is extended or adjusted under 35 U.S.C. 154(b) by 758 days.

(21) Appl. No.: 17/988,283

(22) Filed: Nov. 16, 2022

(65) Prior Publication Data

US 2023/0149164 A1 May 18, 2023

Related U.S. Application Data

(60) Provisional application No. 63/264,220, filed on Nov. 17, 2021.

(51) Int. Cl.
A61F 2/24 (2006.01)

(52) U.S. Cl.
CPC ............ *A61F 2/243* (2013.01); *A61F 2/2436* (2013.01)

(58) Field of Classification Search
CPC .......... A61F 2/95; A61F 2/966; A61F 2/9661; A61F 2/2436; A61F 2/243
See application file for complete search history.

(56) References Cited

U.S. PATENT DOCUMENTS

| | | | | |
|---|---|---|---|---|
| 5,415,664 A | * | 5/1995 | Pinchuk ..................... | A61F 2/95 606/198 |
| 7,235,093 B2 | * | 6/2007 | Gregorich ............... | A61F 2/958 623/1.11 |
| 7,264,632 B2 | * | 9/2007 | Wright ...................... | A61F 2/95 623/1.11 |
| 7,763,063 B2 | * | 7/2010 | Arbefeuille ............... | A61F 2/90 623/1.11 |

(Continued)

FOREIGN PATENT DOCUMENTS

| | | |
|---|---|---|
| EP | 1819304 A2 | 8/2007 |
| EP | 2349095 A1 | 8/2011 |

(Continued)

OTHER PUBLICATIONS

"International Application Serial No. PCT US2022 050081, Invitation to Pay Additional Fees mailed Jan. 25, 2023", 2 pgs.

(Continued)

*Primary Examiner* — Alvin J Stewart
(74) *Attorney, Agent, or Firm* — Morrison & Foerster LLP

(57) ABSTRACT

A prosthesis delivery catheter has an inner distal capsule shaft and a distal capsule configured to house the prosthesis. An anchor catheter with an anchor hub is slidably disposed over the inner distal capsule shaft. An elbow catheter is slidably disposed over the anchor catheter, and a peg plate assembly is adjacent the anchor hub. The peg plate assembly has a plurality of protruding pegs and a plate which form a closed configuration with the pegs abutting the plate, and an open configuration where a gap is between the pegs and plate allowing release of a tether.

45 Claims, 18 Drawing Sheets

(56) References Cited

U.S. PATENT DOCUMENTS

| | | | | |
|---|---|---|---|---|
| 8,414,644 B2 * | 4/2013 | Quadri | A61F 2/2409 | 623/2.11 |
| 8,414,645 B2 * | 4/2013 | Dwork | A61F 2/2436 | 623/2.11 |
| 8,475,523 B2 * | 7/2013 | Duffy | A61F 2/2436 | 623/2.11 |
| 8,562,663 B2 * | 10/2013 | Mearns | A61F 2/2412 | 623/2.11 |
| 10,631,984 B2 * | 4/2020 | Nyuli | A61F 2/2418 | |
| 10,856,982 B2 * | 12/2020 | Perszyk | A61F 2/243 | |
| 10,856,984 B2 * | 12/2020 | Lane | A61F 2/2445 | |
| 11,337,802 B2 * | 5/2022 | Hariton | A61F 2/243 | |
| 11,337,806 B2 * | 5/2022 | Perszyk | A61F 2/2436 | |
| 11,779,742 B2 * | 10/2023 | Chalekian | A61M 39/20 | 604/167.03 |
| 11,998,447 B2 * | 6/2024 | Jackson | A61F 2/2436 | |
| 12,053,380 B2 * | 8/2024 | Hammer | A61F 2/2436 | |
| 12,109,111 B2 * | 10/2024 | Nyuli | A61M 25/0074 | |
| 12,161,552 B2 * | 12/2024 | Deem | A61F 2/2436 | |
| 12,396,851 B2 * | 8/2025 | Hariton | A61F 2/2409 | |
| 2006/0025844 A1 * | 2/2006 | Majercak | A61F 2/95 | 623/1.11 |
| 2008/0065011 A1 * | 3/2008 | Marchand | A61F 2/2436 | 604/103.05 |
| 2011/0319989 A1 | 12/2011 | Lane et al. | | |
| 2013/0274870 A1 * | 10/2013 | Lombardi | A61F 2/2427 | 623/2.11 |
| 2014/0012369 A1 * | 1/2014 | Murry, III | A61F 2/2436 | 623/2.11 |
| 2014/0067050 A1 * | 3/2014 | Costello | A61F 2/2436 | 623/2.11 |
| 2014/0088680 A1 * | 3/2014 | Costello | A61F 2/2436 | 623/1.2 |
| 2014/0155990 A1 * | 6/2014 | Nyuli | A61F 2/243 | 623/2.11 |
| 2014/0172086 A1 * | 6/2014 | Quadri | A61F 2/243 | 623/2.38 |
| 2014/0200649 A1 * | 7/2014 | Essinger | A61F 2/2436 | 623/2.11 |
| 2014/0214153 A1 * | 7/2014 | Ottma | A61F 2/2436 | 623/2.11 |
| 2014/0243959 A1 * | 8/2014 | Nelson | A61F 2/2436 | 623/2.11 |
| 2014/0371848 A1 * | 12/2014 | Murray, III | A61F 2/2418 | 623/2.11 |
| 2015/0306358 A1 * | 10/2015 | Duffy | A61F 2/95 | 604/95.01 |
| 2015/0342736 A1 * | 12/2015 | Rabito | A61F 2/2436 | 623/2.11 |
| 2017/0128206 A1 * | 5/2017 | Rafiee | A61F 2/2418 | |
| 2017/0165064 A1 | 6/2017 | Nyuli et al. | | |
| 2018/0049873 A1 * | 2/2018 | Manash | A61M 25/09 | |
| 2018/0116790 A1 | 5/2018 | Ratz et al. | | |
| 2019/0374342 A1 * | 12/2019 | Gregg | A61F 2/2439 | |
| 2020/0054335 A1 * | 2/2020 | Hernandez | A61B 17/1227 | |
| 2020/0146814 A1 * | 5/2020 | Fung | A61F 2/2436 | |
| 2020/0281720 A1 * | 9/2020 | Jackson | A61F 2/2436 | |
| 2020/0306040 A1 | 10/2020 | Fung et al. | | |
| 2020/0368514 A1 * | 11/2020 | Chalekian | A61M 39/06 | |
| 2021/0378852 A1 * | 12/2021 | Murray, III | A61F 2/9661 | |
| 2023/0024690 A1 * | 1/2023 | Cohen | A61F 2/243 | |
| 2023/0093867 A1 * | 3/2023 | O'Connor | A61F 2/9661 | 623/2.11 |
| 2024/0164901 A1 * | 5/2024 | Kyne | A61F 2/2418 | |
| 2024/0198045 A1 * | 6/2024 | Pfeiffer | A61F 2/95 | |
| 2024/0407936 A1 * | 12/2024 | Murray, III | A61F 2/9661 | |
| 2025/0235312 A1 * | 7/2025 | Kyne | A61F 2/2436 | |

FOREIGN PATENT DOCUMENTS

| | | | |
|---|---|---|---|
| EP | 2349097 A1 | 8/2011 | |
| EP | 2698129 A1 | 2/2014 | |
| EP | 2793749 A1 | 10/2014 | |
| EP | 2919712 A1 | 9/2015 | |
| EP | 2948103 A2 | 12/2015 | |
| EP | 2959866 A1 | 12/2015 | |
| EP | 2967858 A2 | 1/2016 | |
| EP | 3052611 A1 | 8/2016 | |
| EP | 3079633 A1 | 10/2016 | |
| EP | 3102150 A1 | 12/2016 | |
| EP | 3158975 A1 | 4/2017 | |
| EP | 3175823 A1 | 6/2017 | |
| EP | 3277221 A1 | 2/2018 | |
| EP | 3307208 A1 | 4/2018 | |
| EP | 3311775 A1 | 4/2018 | |
| EP | 3340932 A1 | 7/2018 | |
| EP | 3344158 A1 | 7/2018 | |
| EP | 3361991 A1 | 8/2018 | |
| EP | 3410984 A1 | 12/2018 | |
| EP | 3427695 A1 | 1/2019 | |
| EP | 3409454 A4 | 2/2019 | |
| EP | 3443937 A1 | 2/2019 | |
| EP | 3449969 A1 | 3/2019 | |
| EP | 3454795 A1 | 3/2019 | |
| EP | 3490657 A1 | 6/2019 | |
| EP | 3517075 A1 | 7/2019 | |
| EP | 3545905 A1 | 10/2019 | |
| EP | 3549556 A1 | 10/2019 | |
| EP | 3563799 A1 | 11/2019 | |
| EP | 3563806 A1 | 11/2019 | |
| EP | 3570779 A1 | 11/2019 | |
| EP | 3600156 A1 | 2/2020 | |
| EP | 3606443 A1 | 2/2020 | |
| EP | 3661429 A1 | 6/2020 | |
| EP | 3758651 A1 | 1/2021 | |
| EP | 3886763 A1 | 10/2021 | |
| EP | 3912595 A1 | 11/2021 | |
| EP | 3962415 A1 | 3/2022 | |
| EP | 4014928 A1 | 6/2022 | |
| EP | 3220857 B1 | 9/2022 | |
| EP | 3645065 B1 | 9/2022 | |
| EP | 3737336 B1 | 9/2022 | |
| EP | 2104470 B1 | 10/2022 | |
| EP | 2536353 B1 | 10/2022 | |
| EP | 2991588 B1 | 10/2022 | |
| EP | 3043755 B1 | 10/2022 | |
| EP | 3288491 B1 | 10/2022 | |
| EP | 3466373 B1 | 10/2022 | |
| EP | 3552585 B1 | 10/2022 | |
| EP | 3791828 B1 | 10/2022 | |
| EP | 3914191 B1 | 10/2022 | |
| EP | 2538882 B1 | 11/2022 | |
| EP | 2698129 B1 | 11/2022 | |
| EP | 2959866 B1 | 11/2022 | |
| EP | 3175823 B1 | 11/2022 | |
| EP | 3280358 B1 | 11/2022 | |
| EP | 3340923 B1 | 11/2022 | |
| EP | 3478224 B1 | 11/2022 | |
| EP | 3490659 B1 | 11/2022 | |
| EP | 3744291 B1 | 11/2022 | |
| WO | WO-2023058023 A1 * | 4/2023 | A61F 2/9662 |
| WO | 2023091471 | 5/2023 | |

OTHER PUBLICATIONS

"International Application Serial No. PCT US2022 050081, International Search Report mailed Mar. 27, 2023", 4 pgs.
"International Application Serial No. PCT US2022 050081, Written Opinion mailed Mar. 27, 2023", 6 pgs.
Extended European Search Report and Opinion for European Patent Application No. 22896412.8 mailed Sep. 15, 2025, 8 pages.

* cited by examiner

SYSTEMS AND METHODS FOR DEPLOYING AND RETRIEVING A PROSTHESIS

CLAIM OF PRIORITY

The present application is a non-provisional of, and claims the benefit of U.S. Provisional Patent Application No. 63/264,220 filed on Nov. 17, 2021; the entire contents of which are incorporated herein by reference.

CROSS-REFERENCE TO RELATED PATENT DOCUMENTS

This patent application is also related to U.S. patent application Ser. Nos. 13/096,572; 15/379,748; 16/678,364; 16/837,884; and 16/811,693; the entire contents of each of these applications is incorporated herein by reference.

BACKGROUND

Failure of cardiac valves in humans results in blood regurgitating in an upstream or retrograde direction through the heart valve. The heart must work harder to compensate for the inefficient pumping which can cause a host of morbidities including heart failure which can result in death.

There are numerous treatments for addressing incompetent heart valves such as surgical repair and newer less invasive procedures are being adopted such as transcatheter or transapical procedures where a prosthesis is delivered percutaneously thorough the patient's vasculature to the heart where the prosthesis may be delivered to repair or replace the defective native valve. A delivery system may be used to deliver the prosthesis to the target treatment region accurately and safely.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Failure of cardiac valves in humans results in blood regurgitating in an upstream or retrograde direction through the heart valve. The heart must work harder to compensate for the inefficient pumping which can cause a host of morbidities including heart failure which can result in death.

There are numerous treatments for addressing incompetent heart valves such as surgical repair and newer less invasive procedures are being adopted such as transcatheter or transapical procedures where a prosthesis is delivered percutaneously thorough the patient's vasculature to the heart where the prosthesis may be delivered to repair or replace the defective native valve.

Surgical repairs require many hours of meticulous surgery in an operating room, and the patient may need many weeks to recover. Newer transcatheter or transapically delivered devices are promising and allow a much faster recovery. However, it can be challenging to accurately deliver a prosthesis to the target treatment area and once a prosthesis is deployed, if it is not perfectly delivered to the native anatomy may require surgery to remove and replace or to reposition the prosthesis. Therefore, it would be advantageous to provide delivery systems that can deliver a prosthesis or other device to a target treatment region such as the heart more accurately as well as allow the prosthesis to be at least partially or even fully recaptured after deployment in order to allow proper positioning or other adjustments. At least some of these challenges are addressed by the examples disclosed herein.

While the disclosure herein primarily is directed toward delivery systems for prosthetic mitral valves deployed in a native mitral valve, this is not intended to be limiting and the delivery systems and prostheses may be used in other areas of the heart including other valves such as the aortic valve, tricuspid valve, pulmonary valve, or other regions of the heart such as the right atrium, right ventricle, left atrium, or left ventricle. Additionally, the prostheses and delivery systems disclosed herein may be used in regions other than the heart such as the vasculature (e.g. arteries or veins), or other organs, body passageways or any other region of the body.

System for Delivering a Prosthesis

Figure 1:
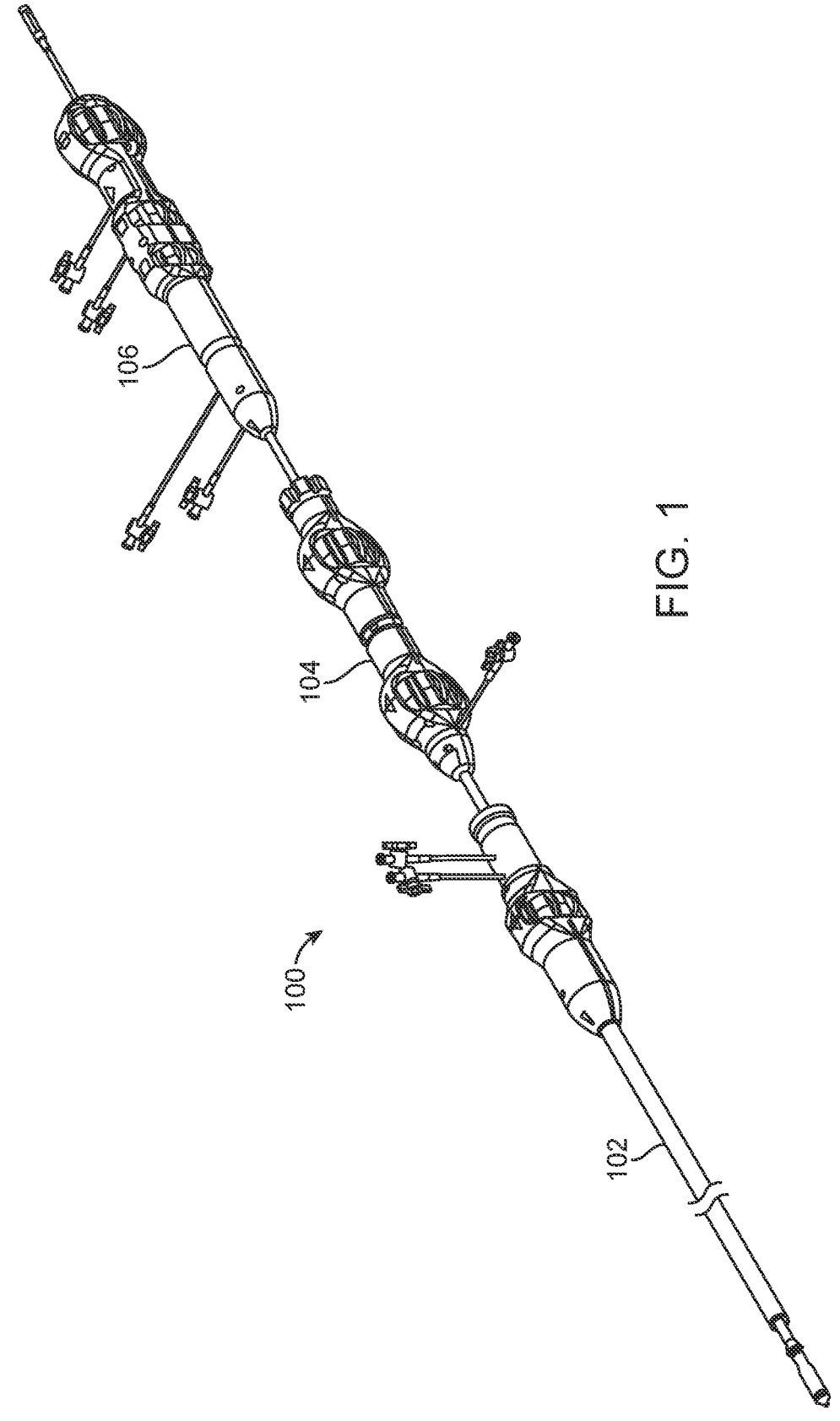
FIG. 1 shows an example of a system for delivering a prosthesis.

FIG. 1 shows an example of a system 100 for delivering a prosthesis. The major elements of the system include an optional introducer sheath 102, an optional steering catheter 104, and a prosthesis delivery catheter 106.

Aspects of the introducer sheath 102, steering catheter 104, and delivery catheter 106 are described in US Pat. Publication Nos. 2011/0319989; 2017/0165064; 2020/0306040; 2020/0281720; and 2020/0368514 and are not repeated herein for the sake of brevity. These five publications are incorporated herein in their entirety. Any of the features disclosed in these references may be used in combination with or substituted for any of the features disclosed herein. Therefore, any permutation or combination of features disclosed above in the references incorporated herein by reference and disclosed herein may be included in an example of a system which may include an introducer sheath, steering catheter, or delivery catheter.

The introducer sheath 102 is optional and may be used to help introduce the system into a patient's vasculature or other body location if desired and may be used to help orient the steering catheter and delivery catheter relative to the target treatment anatomy. In general, the introducer sheath 102 includes an elongate shaft that has a lumen sized to receive the steering catheter. A handle may be coupled to a proximal portion of elongate shaft on the introducer sheath and may include an optional actuator (e.g. a thumb wheel as illustrated) which may be actuated by an operator to control tension in pull wires extending along the elongate shaft and which are coupled to a distal portion of the introducer sheath. Thus, by controlling tension in the pull wires, the actuator may steer the distal end of the elongate shaft in one or more directions. Side ports with Luer hubs may also be fluidly coupled with the handle to allow irrigation of the various lumens and annular regions to prevent air from being introduced into a patient's body, or to take fluid samples (e.g. blood samples), or for delivery of a therapeutic agent. The proximal end of the handle has port for receiving the steering catheter and delivery catheter. The port may include a hemostasis valve.

The illustrations in this specification primarily focus on the working end of the device. Therefore, disclosure and corresponding illustrations emphasize the appropriate end of the device which is often the distal end. One of skill in the art will appreciate that the shafts, tethers and other features may extend axially along the length of the device toward the appropriate end, often the proximal end, and may be coupled to a handle, housing or other structural element which may include an actuator for controlling movement of the applicable shaft.

Introducer Sheath

Figure 2:
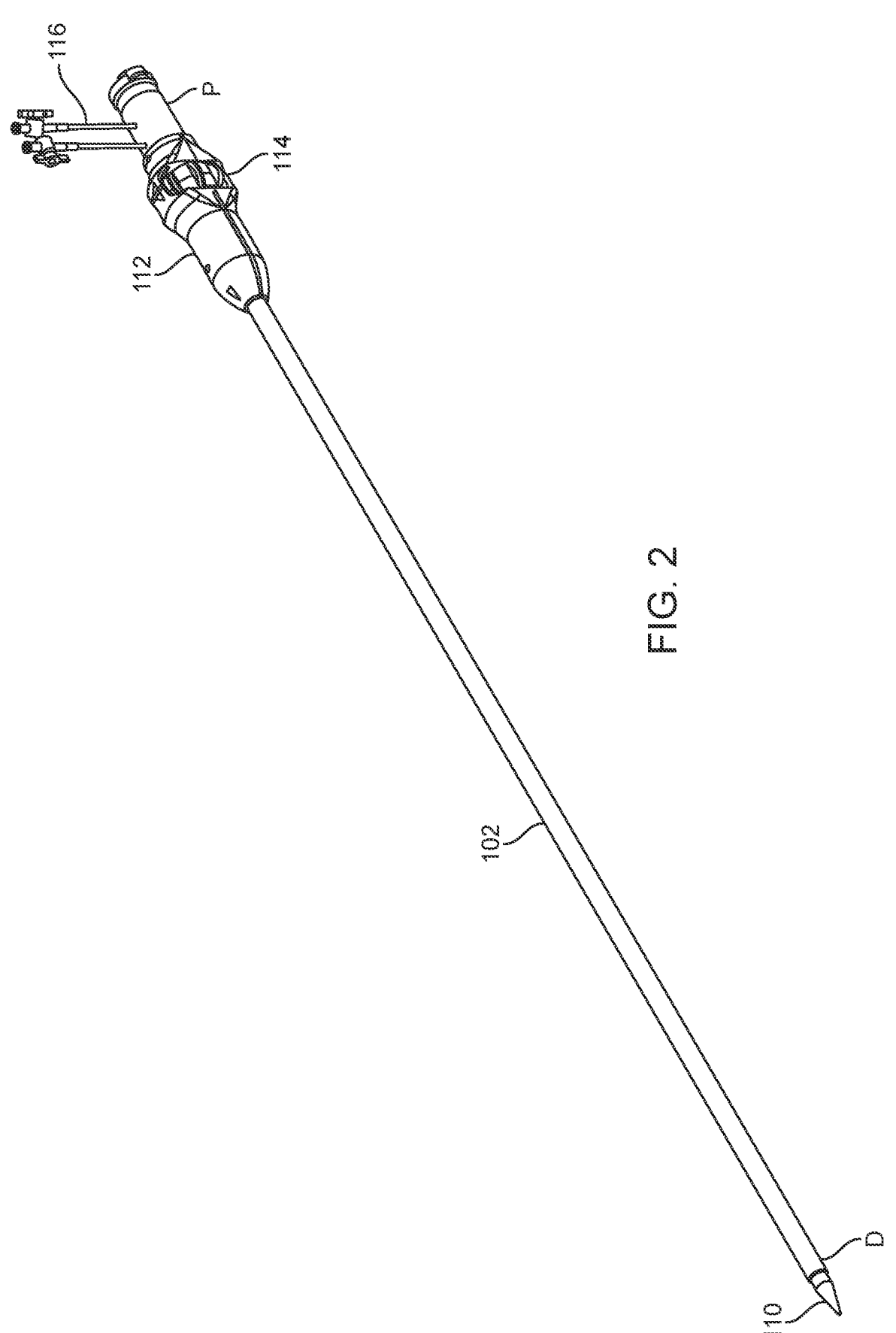
FIG. 2 shows an example of an introducer sheath.

FIG. 2 more clearly illustrates some features of the optional introducer sheath 102. In this example, an optional elongated dilator 110 with a tapered tip is inserted in the introducer sheath to facilitate its insertion into the patient. The tapered tip helps expand and separate tissue to allow introduction of the introducer sheath into the patient. It also adds column strength the introducer sheath to prevent it from buckling during insertion. Once the introducer sheath is positioned, the dilator may be removed. The optional handle 112 may include an actuator 114 as previously discussed above in FIG. 1. Here the actuator is a thumb wheel which may be rotated clockwise or counterclockwise to control the tension in the pull wires (not shown) which actuates the distal tip of the introducer into various shapes. Side ports with Luer connectors 116 may be coupled to the handle for fluid management purposes as previously described. The proximal P and distal ends D of the introducer shaft are also indicated, where the distal end D is typically inserted into the patient while the proximal end is closest to the operator and often disposed outside of the patient.

Figures 3A, 3B:
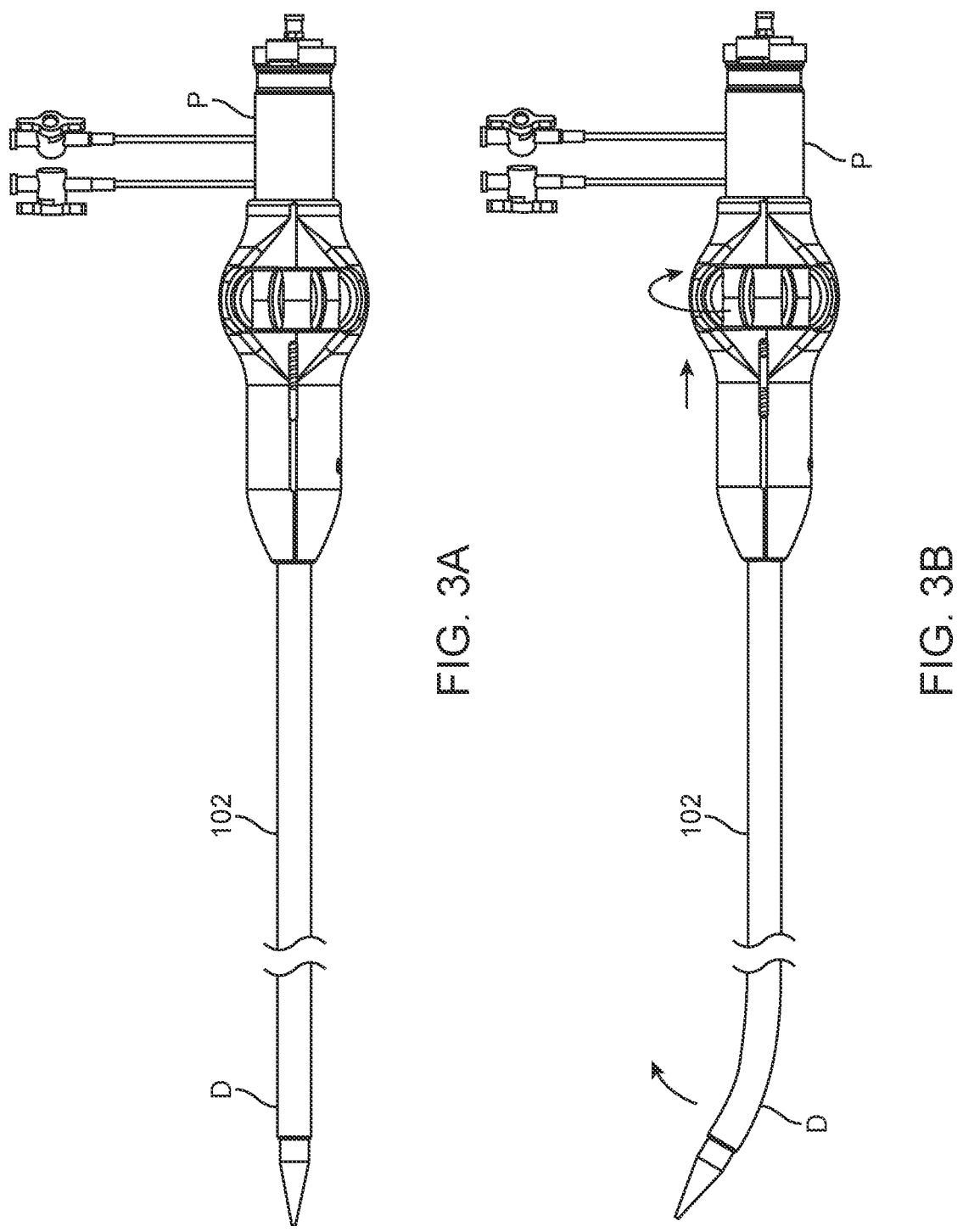
FIGS. 3A-3B show an example of an introducer sheath that may be curved.

FIGS. 3A-3B show an example of an introducer sheath 102 in a linear configuration and a curved configuration after actuation of the actuator.

FIG. 3A shows the introducer sheath 102 in a substantially linear configuration. This may be the unbiased configuration, and when the actuator is actuated, the distal end may be curved into a desired shape as seen in FIG. 3B. Other aspects of the introducer sheath are generally the same as previously described above.

Alternatively, the introducer sheath 102 may be pre-curved in the unbiased configuration, as seen in FIG. 3B, and then the introducer sheath 102 may be straightened out into a biased linear configuration by actuation of the actuator, or by insertion of a rigid straight dilator into the introducer sheath. Thus, the introducer sheath may be straight and then manipulated into a desired curve shape, or it may be pre-formed into a desired curve and then straightened out if desired.

Other aspects of the introducer sheath are disclosed in the US Patent Publications disclosed above and previously incorporated herein in their entirety. Any of the features disclosed in these patent publications may optionally be included with or substituted for any of the features of the introducer sheath disclosed herein.

Figure 4:
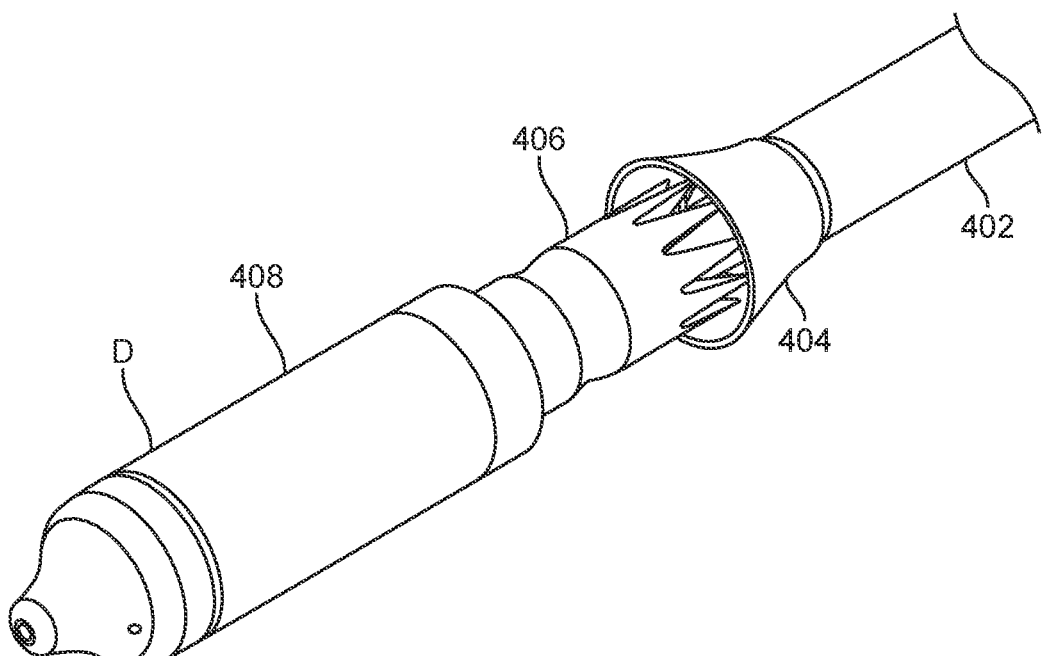
FIG. 4 shows a distal end of a delivery catheter with a prosthesis.

FIG. 4 shows an example of a distal D end of a prosthesis delivery system such as the one illustrated in FIG. 1 above. Here, the distal end D includes a distal capsule 408 which has a central channel or cavity which is sized to house a prosthesis 406 such as a prosthetic cardiac valve including prosthetic mitral valves, prosthetic tricuspid valves, prosthetic aortic valves, prosthetic pulmonary valves, or any other prosthetic valve, or any other prosthesis. In the case of a prosthetic mitral valve, examples of a prosthesis are described in the US Patent Publications disclosed above and incorporated herein by reference. In the example of FIG. 4, the prosthesis is a prosthetic mitral valve with an atrial flange in a collapsed configuration represented by the scalloped or undulating end of the prosthesis 406 which may optionally be described as having a coronate proximal end or castellated end. An outer shaft 402 such as an outer shaft on a steering catheter (e.g. element 104 in FIG. 1) has a flared distal tip that is configured to slide relative to the distal capsule 408 thereby covering or uncovering prosthesis 408. In the situation where prosthesis 408 is a self-expanding prosthesis, removal of the constraint from the prosthesis results in self-expansion of the prosthesis into the target treatment area. In certain situations, this may result in inaccurate placement of the prosthesis. Therefore, various deployment control features that allow more accurate deployment or that permit the prosthesis to be recaptured after partial or full deployment are desirable in order to ensure proper prosthesis placement. Several examples of deployment control features are disclosed herein. They may be used alone, in combination with, or in substitution of any of the features previously disclosed in any of the US Patent Publications incorporated herein by reference.

Shaft Flexibility

Figures 5A, 5B, 5C:
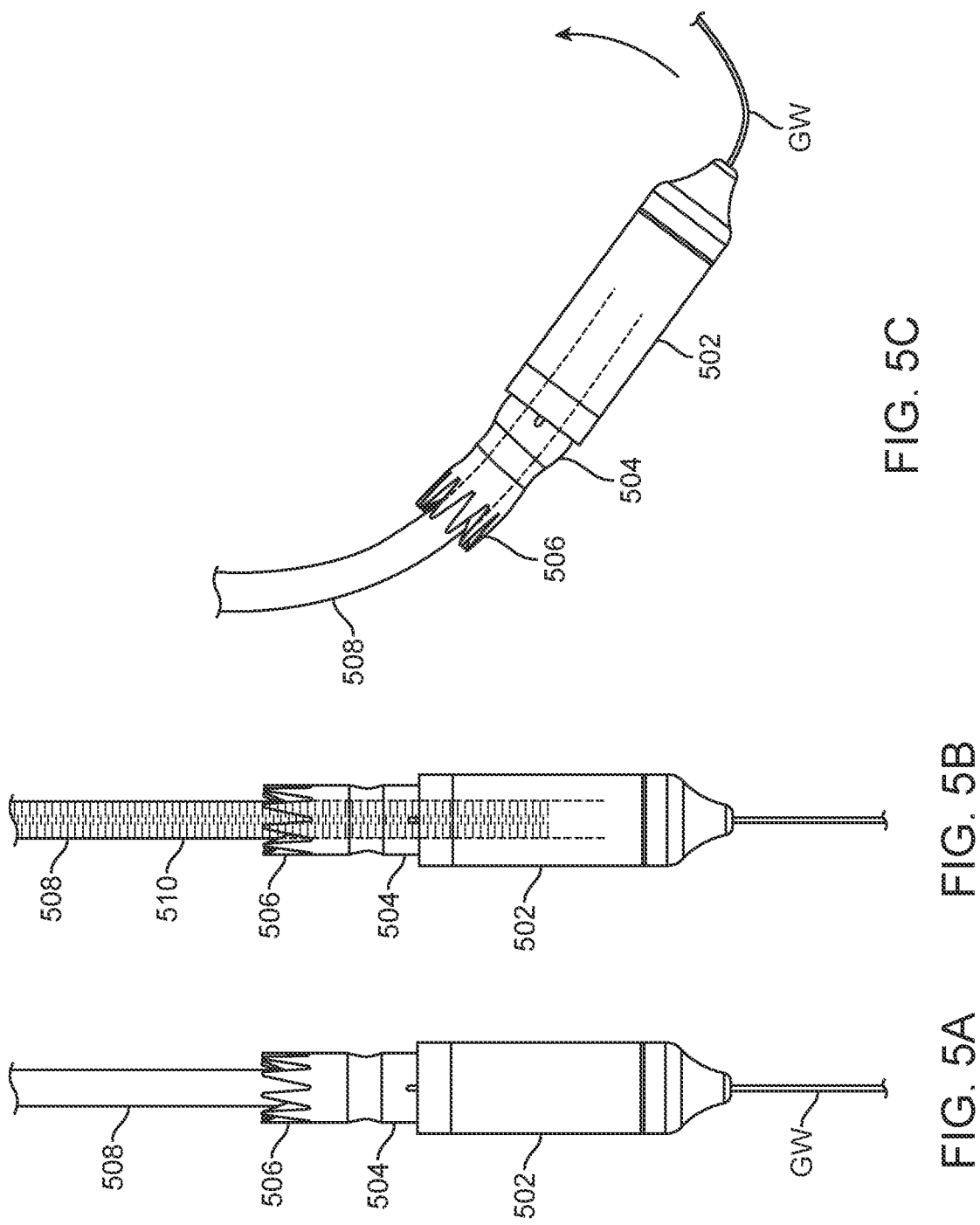
FIGS. 5A-5C show a flexible shaft in a prosthesis delivery system.

FIGS. 5A-5C illustrate an example of shaft flexibility which may be included in any delivery catheter or delivery system. FIG. 5A shows a distal portion of a prosthesis delivery system such as the one illustrated in FIG. 1. Here, a prosthesis 504 is housed in a distal capsule 502 with the atrial flange 506 extending out of the distal capsule and unhoused. An anchor catheter shaft 508 is disposed under the prosthesis and is coupled to the prosthesis further distally (obstructed by the distal capsule and therefore not visible in this view). A guidewire GW extends through a lumen and exits out of the distal end of the capsule.

In order to create a more flexible distal region adjacent the prosthesis, FIG. 5B shows the formation of a plurality of slots 510 in the anchor catheter 508. The slots extend in a direction orthogonal or transverse to the longitudinal axis of the delivery catheter. The slots do not extend all the way through the anchor catheter, otherwise the anchor catheter tip would fall off or have inadequate strength, but the slots extend far enough into the anchor catheter to form a flexible region that allows the distal portion to easily flex during delivery and to accommodate the native anatomy of the target treatment region. The flexible region formed by the slots may be limited to a distal portion of the delivery system adjacent the prosthesis, or the flexible region may extend along any portion or length of the delivery system. Additionally, the slotted region is only shown in the anchor catheter in this example, but the slotted region may be used in any of the shafts of the delivery systems disclosed herein. For example, in the delivery system disclosed in the next set of figures, the delivery system may include five nested catheter shafts. Any one or more of the shafts, or all the shafts may include the slotted flexible region described in FIGS. 5A-5B.

FIG. 5C shows the distal portion of the delivery catheter with the prosthesis bent into a radius due to the flexible region formed by the slotted catheter shaft.

Prosthesis Elbow Tethers

Figure 6A:
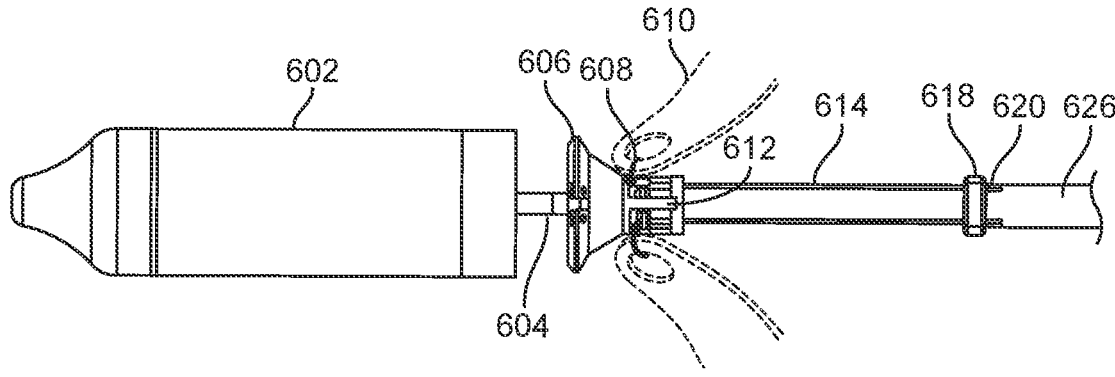
FIGS. 6A-6C show the use of tethers in a prosthesis deployment system.
Figure 6B:
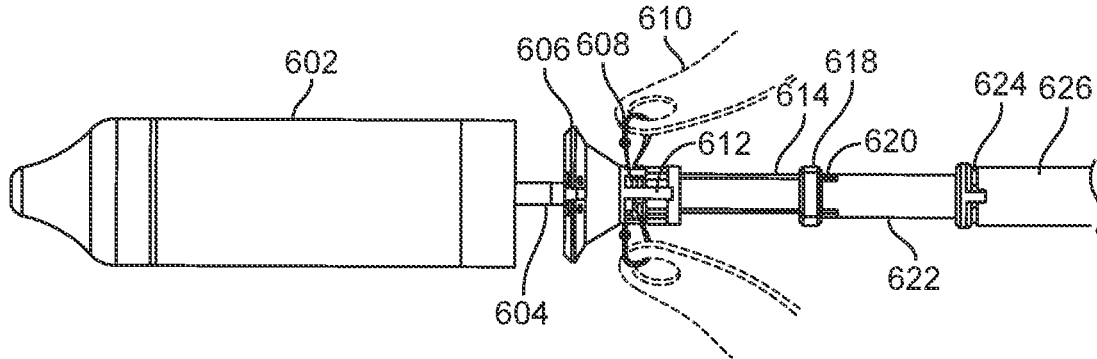
Figure 6C:
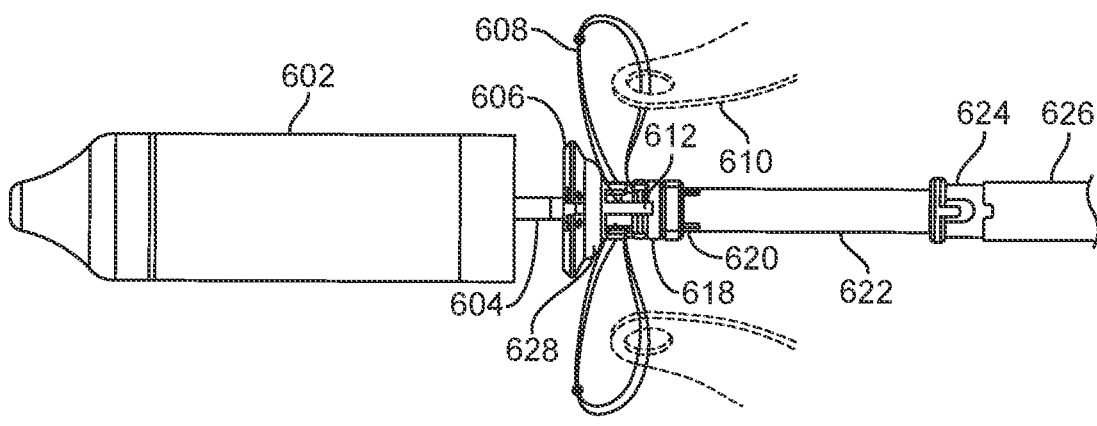

FIGS. 6A-6C illustrate an example of a prosthesis deployment control feature which may be used along with or substituted for any other introducer sheath, steerable catheter or delivery catheter feature disclosed herein. As discussed in the US Patent Publications disclosed above and incorporated herein by reference (e.g. FIG. 9A of US Pat. Pub. No. 2011/0319989), a prosthesis such as a prosthetic mitral valve may have ventricular anchors for helping to anchor the prosthesis to a sub-annular region in the left ventricle. These anchors are tabs with a free end and a fixed end. The fixed end is coupled to the prosthesis and the free ends initially spring open to a horizontal position or a position that is transverse to the longitudinal axis of the prosthesis during initial deployment. An elbow region is also located adjacent the fixed end of the anchor tab that is coupled to the prosthesis. The elbow region remains constrained by an outer sheath or outer shaft during the initial deployment so only the free ends deploy into the horizontal or transverse position and the elbow remains in a collapsed configuration. As the outer sheath or shaft is removed from the elbow, the elbow and the rest of the anchor tab springs radially outward and the free end moves from its horizontal or transverse position to a more upright and vertical position as the elbow springs radially outward. This action can occur rather rapidly as it relies on the springiness of the ventricular anchor, and in certain situations may spring open resulting in improper deployment and anchoring on the sub-annular tissue. Therefore the use of a tether or other control element may facilitate more accurate prosthesis deployment and anchoring. And, in the situation where deployment was not optimal, the use of the tether or other control element may allow retrieval of the anchor tab so that is may be repositioned and redeployed into the correct position.

FIG. 6A shows a tether 608 extending through a hole in the ventricular anchor tab elbow. The tether is coupled to the elbows 610 of a prosthetic valve and in the fully collapsed configuration for delivery. The illustrations in FIGS. 6A-6C have simplified the representation of an elbow and only show a portion of the elbow. Some examples of the elbow would be V-shaped or wishbone shaped with one arm of the V or wishbone forming the free end of the anchor tab, and the other arm of the V or wishbone being connected to the expandable prosthesis frame. This aspect is described in more detail below. Here the delivery catheter includes a distal capsule 602 for housing the prosthesis in a channel in the distal capsule (only the anchor tabs of the prosthesis are shown in this view). The distal capsule 602 is coupled to the distal capsule inner shaft 604. Movement of the inner shaft 604 will move the distal capsule 602 proximally or distally. An anchor hub 606 is an annular structure having a plurality of slots (three in this example) which are substantially parallel with the longitudinal axis of the catheter. The slots are configured to capture and hold a strut on the prosthesis such as a commissure tab. This will be discussed in more detail below. The anchor hub 606 is coupled to an anchor catheter 614 which is slidably disposed over the inner shaft 604. Adjacent the anchor hub is a peg plate assembly 612 which is used to hold the anchor tab tethers as will be described in greater detail below. Tethers 608 are coupled to the peg plate assembly 612 and the ventricular anchor elbow 610 to hold the elbow in a radially collapsed configuration for delivery. When tension in the tether is released and when the tether is released from the peg plate assembly, the anchor tab elbows radially expand and are released from the delivery catheter. An elbow catheter 622 is slidably disposed over the anchor catheter. The tethers are coupled 620 to the elbow catheter, or extend through the elbow catheter to a handle on the proximal end of the delivery catheter where they may be controlled. A ring 618 disposed at the distal end of the elbow catheter 622 may be used to help actuate the peg plate assembly as will be discussed below.

FIG. 6B shows partial release of the prosthesis elbows 610. Here, elbow catheter 622 is advanced distally over anchor catheter 614 so that tension in tether 608 is released slightly. Self-expanding elbows will then radially expand outward and take up any slack in the tension, thereby partially deploying. The tethers are still held by the peg plate assembly 612, therefore if the operator wishes to retract the elbows into a collapsed configuration, the operator may reapply tension to the tethers by proximally retracting elbow catheter 622 to collapse the elbows. FIG. 6B also shows the optional inner and outer lasso catheters 624, 626 which are used to control a lasso coupled to the prosthesis that may be used to control deployment of a superior portion of the prosthesis, such as an atrial flange. The inner and outer lasso catheters form a release mechanism for a lasso. In this figure, the release mechanism is closed. The lasso is described in more detail below.

FIG. 6C shows the elbow catheter 622 fully advanced distally to allow the elbows 610 to fully expand, and the peg plate assembly 612 is now open and the tethers 608 can be released from the peg plate assembly, thereby releasing the elbows from the delivery catheter. Here, the elbow catheter 622 is slidably advanced over the anchor catheter (not visible) until the ring 618 abuts the peg plate assembly 612. This releases all the tension from the tether 608 allowing the elbow 610 to fully expand. When ring 618 is pressed against peg plate assembly 612, resilient spring element 628 is compressed thereby releasing a compressive force against protruding pegs in the peg plate assembly so that a gap is formed between the protruding pegs and a plate. The tether may be released from the peg plate assembly by passing through the gap. This is illustrated more clearly below. The inner and outer lasso catheters may be actuated before or after elbow release as desired depending on the delivery route (e.g. transseptal or transapical). Additional details on the lasso release mechanism were previously disclosed in US Patent Applications disclosed above and incorporated herein by reference. Additional information on the lasso release mechanism is also disclosed below. In this figure, the lasso release mechanism is open, allowing release of the lasso.

Figure 7A:
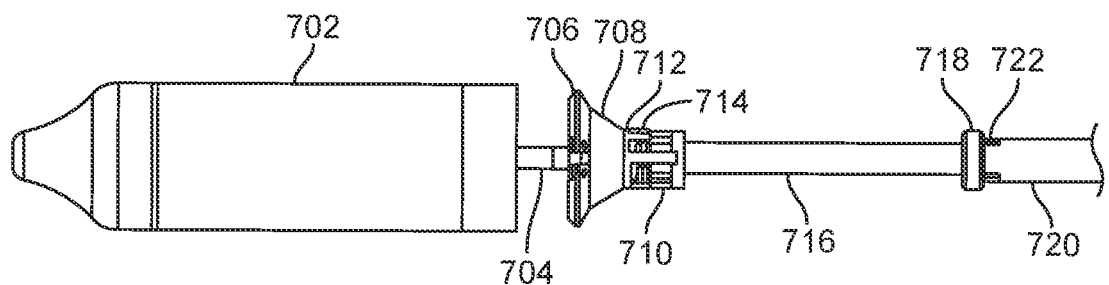
FIGS. 7A-7C show FIGS. 6A-6C in greater detail.
Figure 7B:
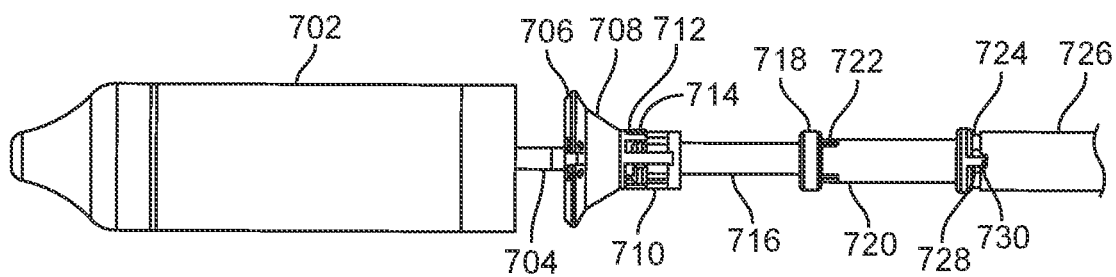
Figure 7C:
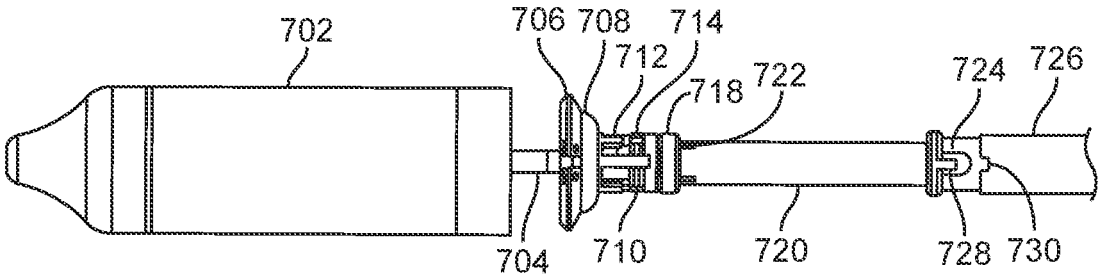

FIGS. 7A-7C more clearly show operation of the various catheter shafts in the example of a prosthesis delivery system previously illustrated in FIGS. 6A-6C. FIGS. 7A-7C do not show the tethers or prosthesis for ease of viewing and convenience.

FIG. 7A shows distal capsule 702 coupled to inner capsule shaft 704. The capsule 702 as previously mentioned has a central channel that is sized to house the prosthesis (not shown). An anchor catheter 716 slides over the inner capsule shaft 704. Coupled to a distal end of the anchor catheter 716 is a hub element 706 which has slots for holding struts on the prosthesis. A peg plate assembly 710 which includes a resilient spring 708, a plurality of protruding pegs 712 and a peg plate 714 is adjacent a distal end of the anchor catheter 716. An elbow catheter 720 is slidably disposed over the anchor catheter 716. Apertures 722 in the elbow catheter allow the elbow tethers to be either coupled to the elbow catheter or to pass through the elbow catheter proximally to a handle (not shown) on the proximal end of the delivery catheter. The handle may be used to control tension in the tethers as well as having a release mechanism for releasing the tethers from the delivery catheter which also allows the tethers to disengage from the prosthesis elbows. An annular ring element 718 coupled to the distal end of the elbow catheter 720 is used as a pusher to abut and move the peg plate assembly. In FIG. 7A, the pegs are engaged with the peg plate so there is no gap therebetween so that the tethers are held by the peg plate assembly. Thus, FIG. 7A represents the configuration where tension is held in the tethers which maintain the prosthesis elbows in a collapsed configuration for delivery.

FIG. 7B shows an intermediate configuration of the delivery catheter between the closed peg plate configuration in FIG. 7A and the open peg plate configuration in FIG. 7C. Here the elbow catheter 720 is advanced over the anchor catheter 716 which releases tension in the tethers (not shown) and thereby allows the prosthesis elbows to partially radially expand. The inner lasso catheter 724 and outer lasso catheter 726 are also visible in this view and both are slidably disposed over the elbow catheter and are involved with controlling the lasso which may optionally be included in a delivery system and used to help control deployment and retrieval of the atrial flange or superior portion of the prosthesis. A protrusion 728 on the inner lasso catheter that is received in a slot 730 on the outer lasso catheter forms a mechanism for capturing the lasso and releasing the lasso, or provides an aperture for the lasso to enter the outer lasso catheter and pass proximally to a control mechanism on a handle coupled to a proximal end of the delivery catheter. 100511 FIG. 7C shows the open configuration of the delivery catheter where the elbow tether may be released from the peg plate assembly. Also, optionally the lasso capture mechanism is also in the open position. In FIG. 7C, the elbow catheter 720 has been advanced further distally so that ring 718 abuts the peg plate assembly 710 which compresses resilient spring element 708. When resilient spring element 708 is in the compressed configuration, it releases a force from the protruding pegs 712 so that they no longer abut the peg plate 714 and form a gap therebetween. Thus, the tether may be released from the delivery catheter and the prosthesis elbows, allowing full radial expansion and decoupling. In the situation where the anchor tabs are not positioned correctly or in an optimal location, before releasing the tether, the tethers may be re-tensioned and collapsed to allow repositioning and once a desired position is achieved, the tethers may be released. Tension may be applied to the tethers by proximally retracting the elbow catheter if the tether is attached thereto, or if the tethers extend through the elbow catheter proximally to a handle on the proximal end of the delivery catheter, then an actuator on the handle may be actuated to apply tension to the tether. FIG. 7C also shows the lasso capture mechanism in an open configuration. Here, the protruding peg 728 on the inner lasso catheter 724 is advanced distally relative to the slot 730 on the outer lasso catheter 726 to form a gap therebetween so that the lasso can be released. As with the tether, the tension on the lasso may be controlled to control deployment of the superior portion of the prosthesis constrained by the lasso, and if needed prior to release of the lasso from the delivery catheter, the lasso may be tensioned again to collapse the superior portion of the prosthesis for repositioning and then the lasso may be released to allow the superior portion of the prosthesis to fully expand and detach from the delivery catheter. Additional details of the lasso capture mechanism are described below.

Figures 8A, 8B:
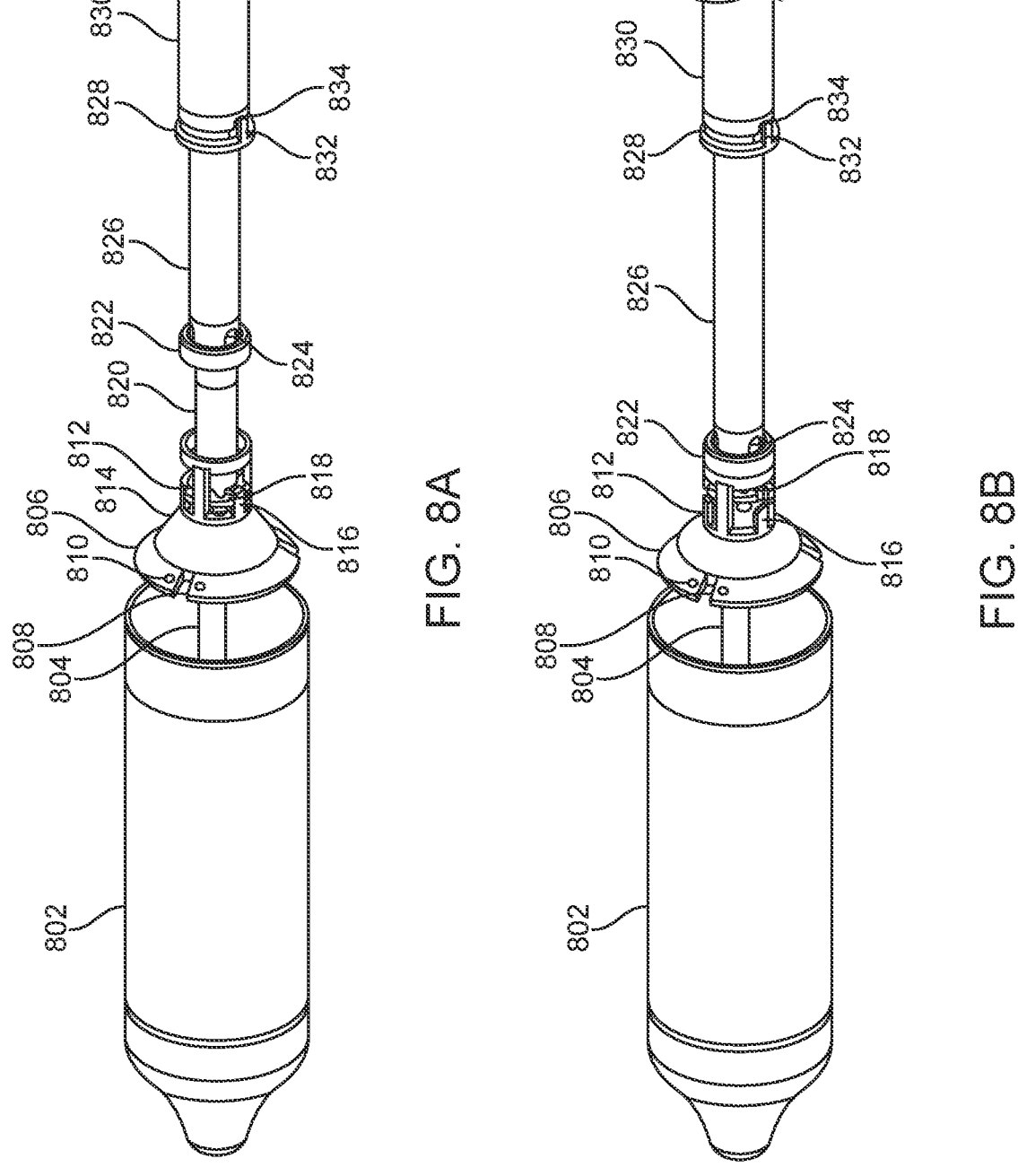
FIGS. 8A-8B show the distal end of the system in FIGS. 6A-6C and 7A-7C.

FIG. 8A shows a close-up of the peg plate assembly in FIGS. 6A-6C and 7A-7C in the closed position, and FIG. 8B shows a close-up of the peg plate assembly in the open position.

FIG. 8A shows the distal portion of the delivery catheter in FIGS. 6A-6C and 7A-7C. Again, a distal capsule 802 is coupled to an inner distal capsule shaft 804. A hub element 806 is coupled to an anchor catheter 820. The hub element includes slots 808 for receiving and holding a strut on the prosthesis (not shown). Alignment apertures 810 allow an operator to align an anterior portion of the prosthesis with the anterior portion of the delivery catheter. A peg plate assembly 812 including a resilient spring element 814, protruding pegs 816 and slots in a peg plate 818 allow a tether to be captured therein or released. An elbow catheter 826 includes a ring element 822 for pressing against the peg plate assembly to compress the spring element 814 and allow formation of a gap between the peg and the peg plate. Apertures 824 in the elbow catheter allow the tether to be coupled to the elbow catheter or to pass through the elbow catheter proximally to a handle. An inner 828 and outer lasso catheter 830 also form a capture mechanism for holding a lasso between a protruding pin or peg 832 and a slot 834. In FIG. 8A, the pegs are engaged with the peg plate to close the gap therebetween to hold the tether.

FIG. 8B shows compression of resilient spring element 814 by pushing the ring 822 distally against the peg plate assembly which allows the protruding pegs to move away from the peg plate thereby forming a gap therebetween which allow the tethers (not show) to be released from the delivery catheter. Other aspects of FIG. 8B are generally the same as in FIG. 8A. The lasso capture mechanism is shown in the closed position, but may be operated independently of the peg plate assembly and therefore may be in the open position.

Figures 9A, 9B:
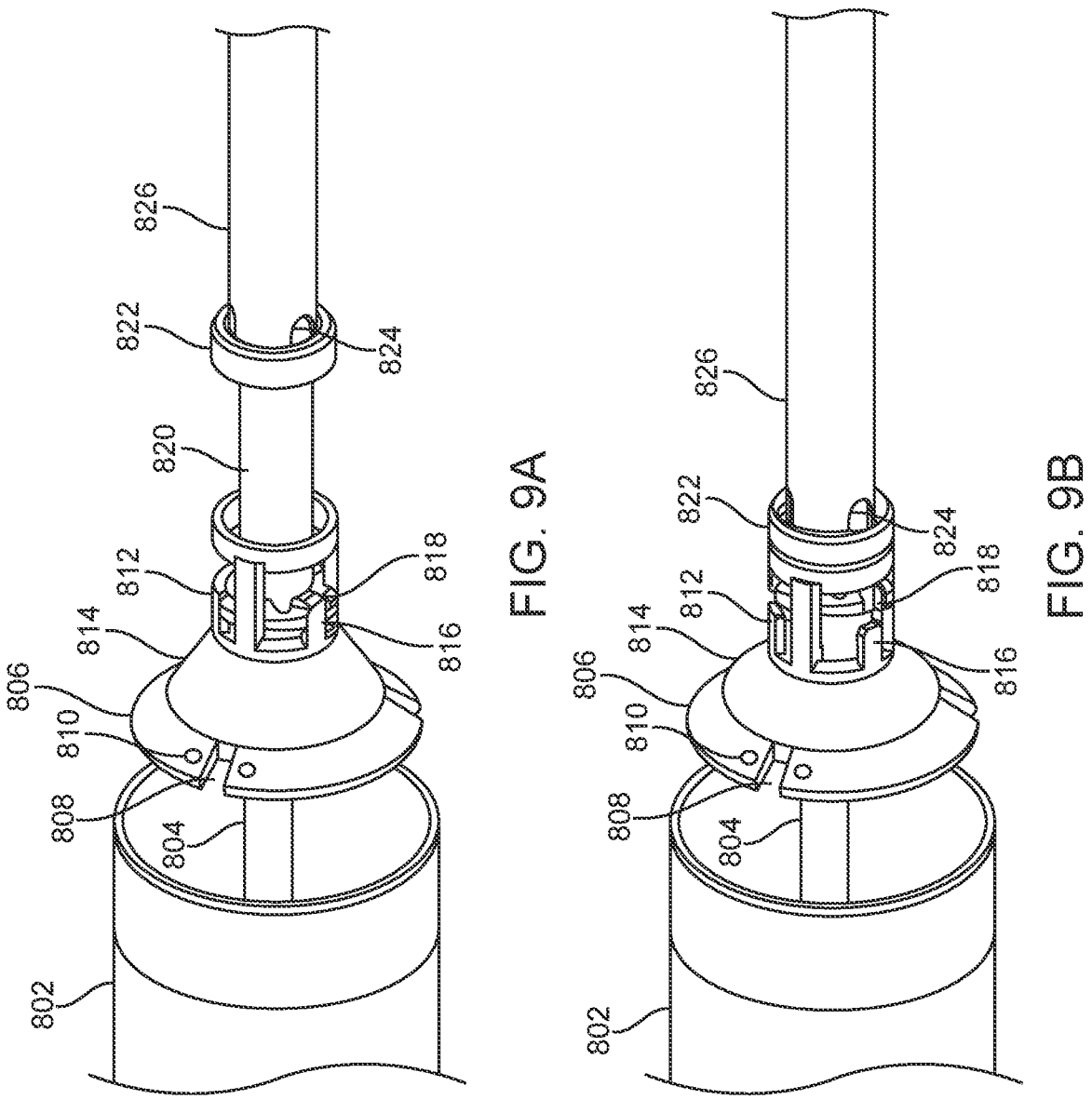
FIGS. 9A-9B show an example of a mechanism for capturing and releasing a tether.

FIG. 9A is an enlarged version of FIG. 8A showing the peg plate assembly in a closed configuration.

FIG. 9B is an enlarged version of FIG. 8B showing the peg plate assembly in an open configuration.

Deployment Control with a Lasso

Figures 10A, 10B, 10C:
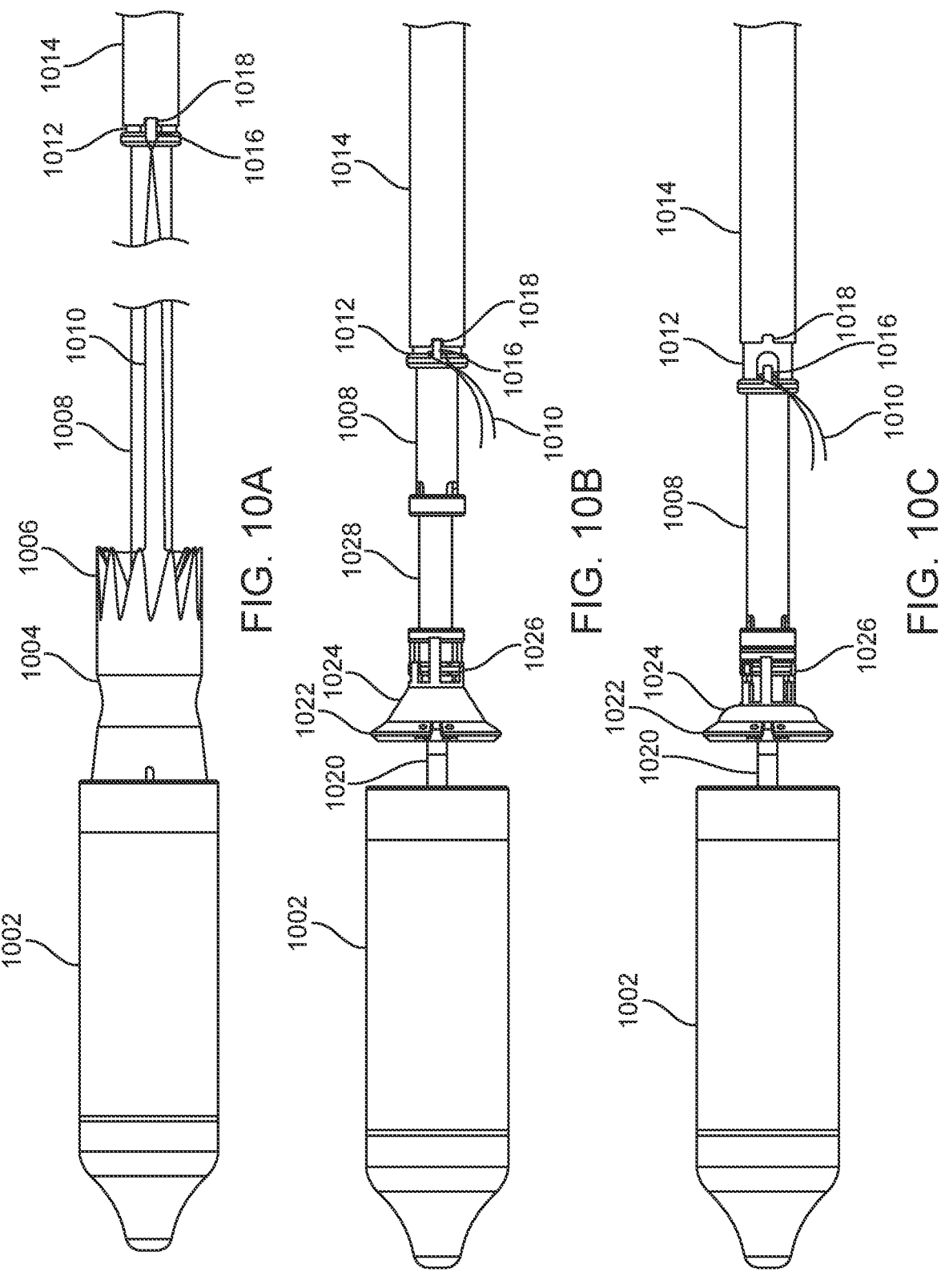
FIGS. 10A-10C show an example of a lasso used to control deployment of a prosthesis.

FIGS. 10A-10C show an example of an optional lasso used to control deployment and retrieval of a prosthesis such as a prosthetic mitral valve.

FIG. 10A shows the distal end of a delivery catheter having a distal capsule 1002 that houses a prosthesis 1004 in a central channel of the capsule, and that is coupled to an inner capsule shaft (not shown). The proximal end of the prosthesis including an atrial flange 1006 remains uncon- strained by the capsule and outside of the distal capsule but constrained by a lasso. One or more lassos 1010 extend circumferentially around the superior portion of the pros- thesis which includes the atrial flange to hold it in a radially collapsed configuration during delivery. The lassos extend along elbow catheter 1008 and are either held by the peg 1016 and slot 1018 on the inner and outer lasso catheters, 1012, 1014, or the lassos extend through the outer lasso catheter to a proximal handle where they may be tensioned, untensioned and held or released. In this example, tension is applied to the lasso 1010 thereby holding the atrial flange in a collapsed configuration.

FIG. 10B shows the delivery catheter with the prosthesis removed for convenience and is generally the same as the example in FIGS. 6A-6C and 7A-7C. In this view, the inner capsule catheter 1020 is shown coupled to the distal capsule 1002. Also the anchor hub 1022, resilient spring 1022 and peg plate assembly 1026 with pegs abutting a plate are also shown and they generally take the same form as previously described in FIGS. 6A-6C and 7A-7C. Also, the anchor catheter 1028 is visible and it is coupled to the anchor hub 1022 and the peg plate assembly is adjacent a distal end of the anchor catheter. The tethers used to hold the anchor tab elbows in a collapsed configuration are not shown in this view where the elbow catheter 1008 is advanced to release tension in the tethers. The lasso 1010 is shown sandwiched or held by the peg 1016 on the inner lasso catheter 1012 which abuts a slot in the outer lasso catheter 1014. When the peg on the inner lasso catheter is moved away from the slot on the outer lasso catheter, a gap between the peg and the slot is created, allowing the lasso to be released therefrom. In another example, the lasso extends through the outer lasso catheter proximally toward a handle on the proximal end of the delivery catheter where a control mechanism may be used to control tension in the lasso as well as to hold or release the lasso from the handle. The inner and/or outer lasso catheters may be advanced distally to release tension on the lasso to allow partial or full expansion of the atrial flange of the prosthesis.

FIG. 10C shows the peg plate assembly 1026 in the open position where the pegs do not abut the plate, thereby forming a gap therebetween which allows the tethers to be released from the peg plate assembly. This configuration is achieved by advancing the elbow catheter 1008 distally until it abuts the peg plate assembly and compresses the resilient spring into a collapse configuration as previously described above. Additionally, the inner lasso catheter 1012 may be advanced distally relative to the outer lasso catheter 1014 so that a gap is formed between peg 1016 and slot 1018 which allows the lasso to be released. Also both inner and outer lasso catheters have been advanced distally to release ten- sion from the lasso to allow the atrial flange of the prosthesis to radially expand. Prior to release of the tethers or the lassos, they may be re-tensioned if desired in order to re-collapse the elbow or atrial flange into a collapsed con- figuration so they may be repositioned if necessary. And once the tethers and lassos have been released from the delivery catheter, the prosthetic valve is unattached to the delivery catheter and the delivery catheter may be removed from the patient leaving the prosthesis behind.

The lasso may be used to help control deployment of an atrial flange as disclosed in US Pat. Pub. No. 2020/0306040 previously incorporated herein by reference. A second lasso, or a lasso extending around the atrial flange with a second circumferential loop around a more inferior portion of the atrial portion of the prosthesis may also be used if additional control of the atrial flange and atrial portion of the prosthesis is desired.

Figure 11:
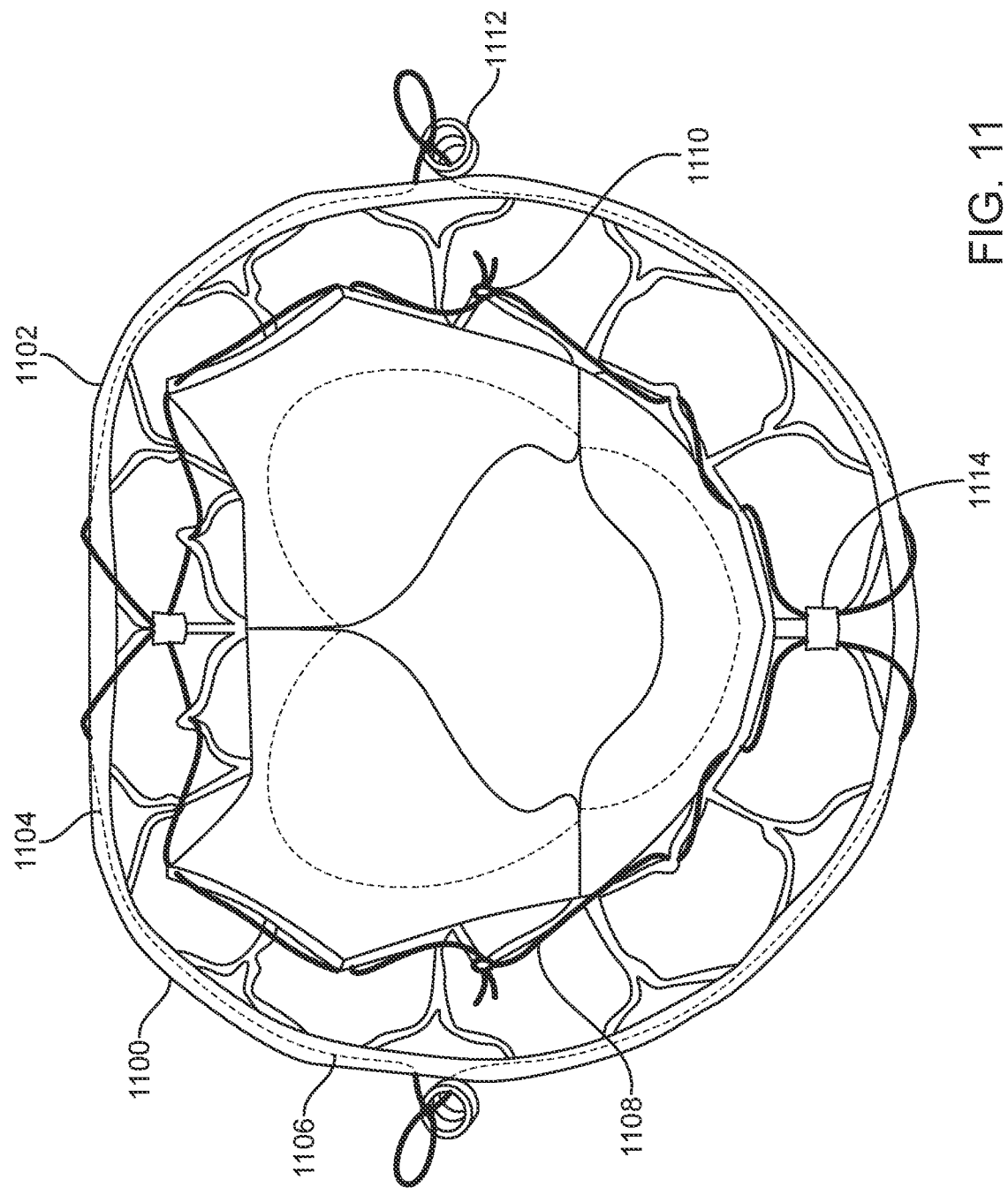
FIG. 11 shows an example of a lasso used to control deployment of a prosthesis.

FIG. 11 shows a single continuous lasso with two loops that may be used to control two regions of the atrial portion of a prosthesis such as a prosthetic mitral valve. This illustration is a top view (from the atrial end down toward the ventricular end of the prosthesis) of a prosthetic mitral valve 1100 in the expanded configuration. The atrial flange 1102 is fully expanded. A first loop 1106 in the lasso 1104 is coupled to and extends circumferentially around the atrial flange 1102. The lasso also continues and has a lower loop 1108 which is coupled to and circumferentially extends around an inferior portion of the atrial portion of the prosthesis. The lasso may be coupled to rings 1112 on the atrial flange or the lasso may be woven into the struts of the prosthesis frame. Optional collars may also be used to couple the lasso to the prosthesis. Also the struts may be tied 1110 to the prosthesis frame if desired or multiple filaments tied together, or a single continuous filament may be used. In this example, the upper loop of the lasso controls expan- sion of the atrial flange and the lower loop of the lasso controls expansion of an inferior portion of the atrial portion of the prosthesis. Again, release of tension in the lasso allows the atrial portion to radially expand, and application of tension collapses the atrial portion or holds the atrial portion in a collapsed configuration. Thus, if the prosthesis is not deployed properly, the atrial portion may be re- collapsed and repositioned if needed.

Examples of Deployment

FIGS. 12A-12H illustrate an example of transseptal deployment of a prosthetic mitral valve using the deploy- ment control mechanisms disclosed herein. This is not intended to be limiting and other delivery routes are possible such as transapical. This example includes both lassos for controlling atrial deployment of the prosthesis as well as elbow tethers for controlling ventricular anchor tab deploy- ment. The atrial lasso is optional and the ventricular tethers are also optional.

Figures 12A, 12B, 12C, 12D:
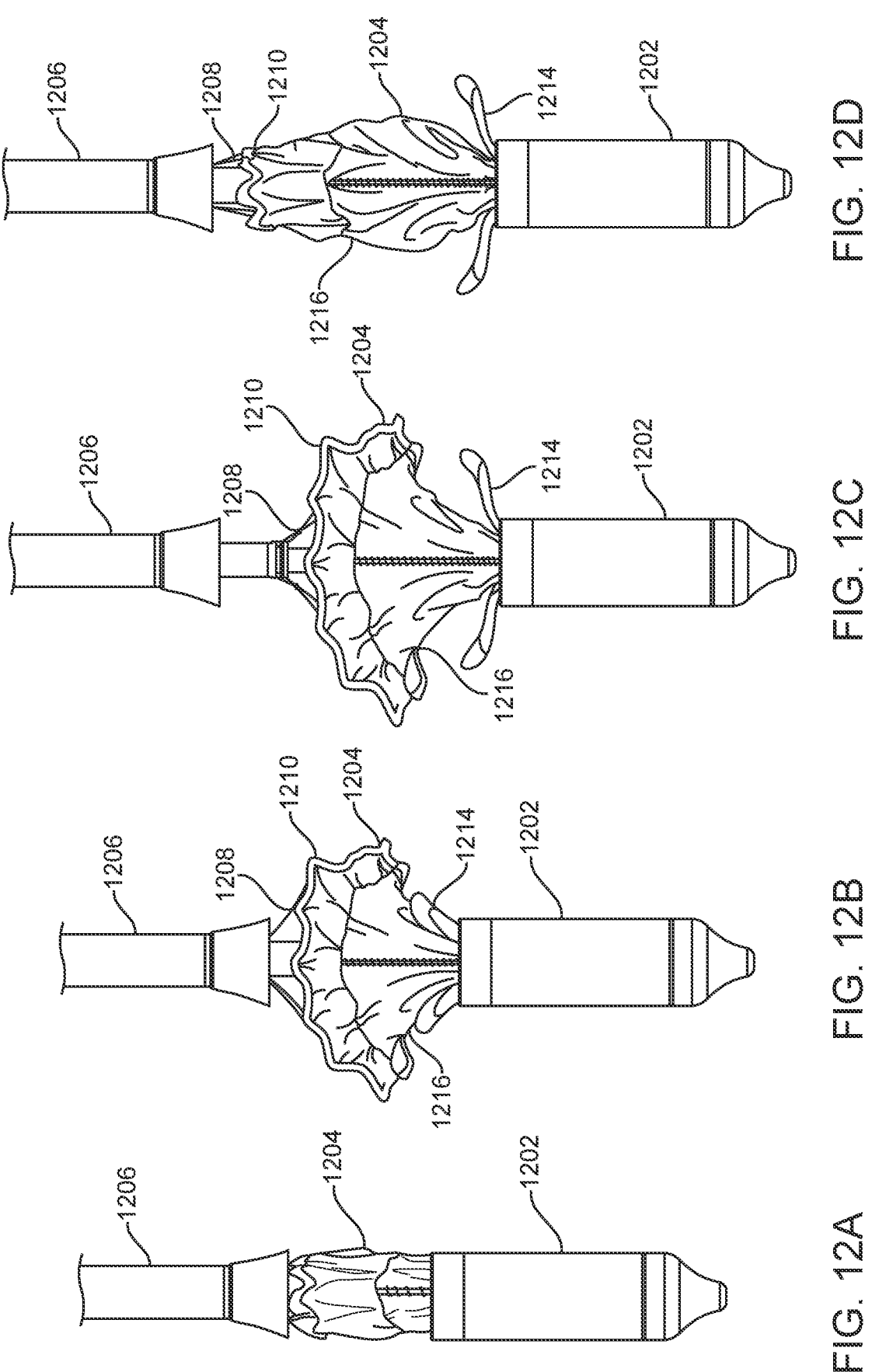
FIGS. 12A-12H show an example of deployment of a prosthesis using a tether and/or a lasso control mechanism.

FIG. 12A shows a delivery catheter with a prosthetic mitral valve 1204 in the undeployed configuration. The prosthesis 1202 is partially housed in the distal capsule 1202, and the flared end of the steering catheter 1206 is adjacent the atrial skirt after the distal capsule has been advanced slightly distally.

FIG. 12B shows the distal capsule 1202 slightly advanced distally to allow partial expansion of the ventricular anchor tabs 1214 as well as partial expansion of the annular portion 1216 and atrial portion 1210 of the prosthesis. The distal capsule still constrains the elbows of the ventricular anchor tabs thereby keeping them in a radially collapsed configu- ration while free ends expand outward partially. A lasso 1208 keeps the atrial flange from fully deploying.

FIGS. 12C shows further distal advancement of the cap- sule 1202 allows the prosthesis 1204 to continue to expand. The ventricular anchor tabs 1214 continue to open up so the free ends are almost horizontal or otherwise transverse to the longitudinal axis of the delivery catheter while the elbows are still constrained by the capsule and also held by tethers. Additionally, as tension is released from the lasso 1208, the annular portion 1216 and atrial flange on the atrial portion 1210 of the prosthesis also continues to expand but is still constrained by the lasso and coupled to the delivery catheter.

If the prosthesis has not deployed correctly or is not positioned correctly, the prosthesis may be retrieved as seen in FIG. 12D. Here, tension is re-applied to the lasso 1208 in order to collapse the atrial flange 1210 and annular portion 1216 of the prosthesis 1204. The ventricular anchors 1214 may also be re-collapsed if needed by retracting them into the distal capsule and/or by tensioning the elbow tethers, but this is not illustrated in FIG. 12D. Once the prosthesis has been re-collapsed, it may be repositioned and re-oriented into a desired location at the target treatment site which may be a native mitral valve.

Figures 12E, 12F, 12G, 12H:
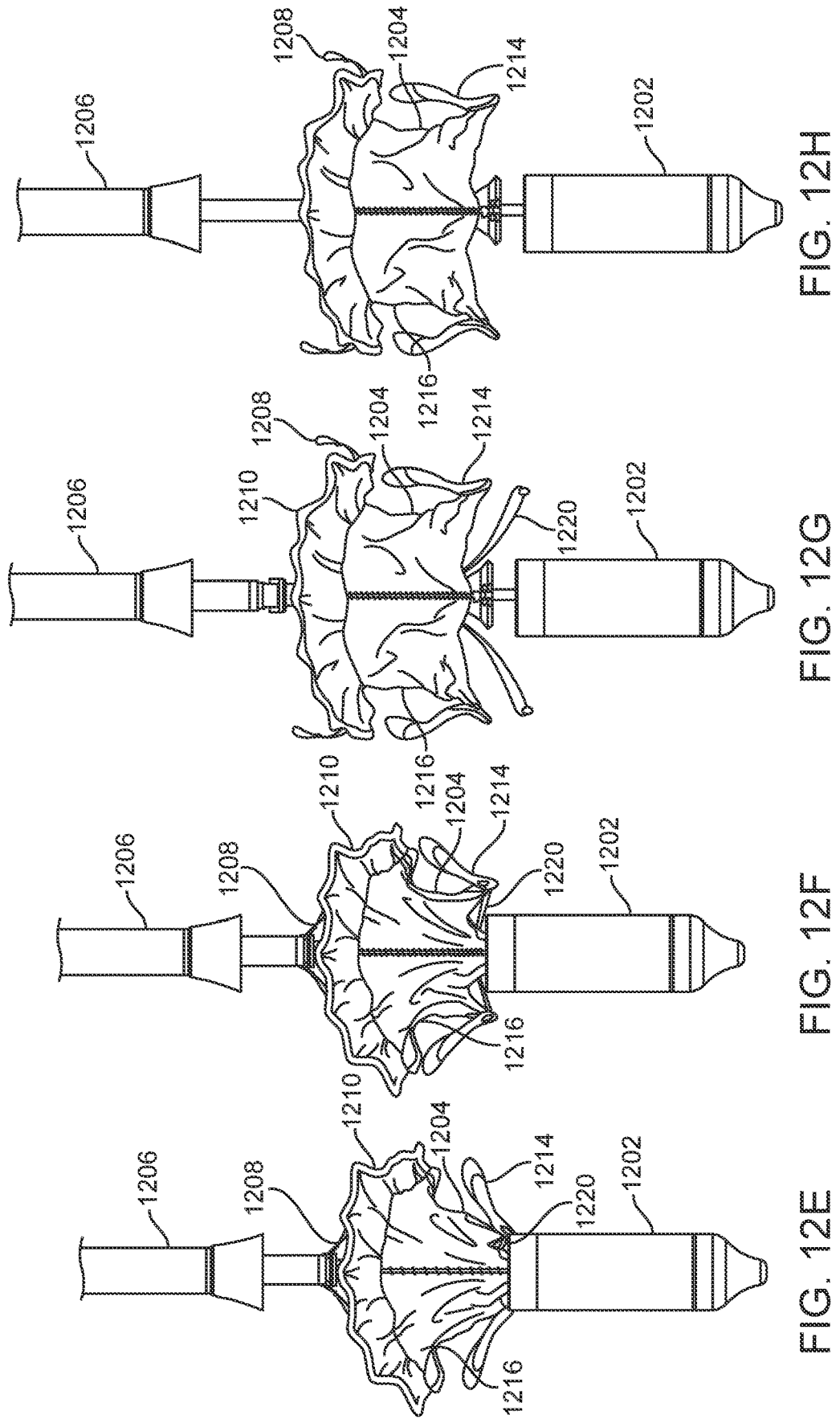

Once repositioned, FIG. 12E shows that release of tension in the lasso 1208 thereby allows the atrial flange in the atrial portion 1210 of the prosthesis 1204 to open up again. The distal capsule 1202 may also be further advanced distally so that the ventricular anchor tab 1214 elbows are not constrained by the distal capsule 1202 but they are held in place by the tether 1220.

FIG. 12F shows the prosthesis 1204 expanded. The ventricular anchors 1214 are expanded and released from the distal capsule but the elbows are still tethered and coupled to the delivery catheter. Similarly the atrial flange of the atrial portion 1210 is expanded but still coupled by a lasso 1208 to the delivery catheter. Also the commissure tabs (not shown in this view) are still coupled to the slots in the hub (also referred to as the anchor) on the hub catheter (also referred to as the anchor catheter). If recapture of the prosthesis and repositioning is required, this is still possible.

FIG. 12G shows release of the prosthesis 1204 from the delivery catheter. Here the lasso 1208 is released from the delivery catheter as previously described above and the elbow tether 1220 is also released from the delivery catheter as previously described. Also the commissure posts are released from the anchor hub. Thus, the ventricular anchors move from a horizontal or transverse position (relative to the longitudinal axis of the prosthesis) to a more vertical position that is substantially parallel with the longitudinal axis of the prosthesis. And the atrial flange is fully expanded.

FIG. 12H shows retraction of some of the shafts of the delivery catheter proximally away from the prosthesis. The remaining shafts may then also be retracted through the prosthesis and removed from the patient with the prosthetic valve implanted and anchored into the native valve.

FIGS. 13A-13F show an example of transapical prosthesis deployment using any of the deployment control mechanisms disclosed herein.

Figures 13A, 13B, 13C, 13D, 13E, 13F:
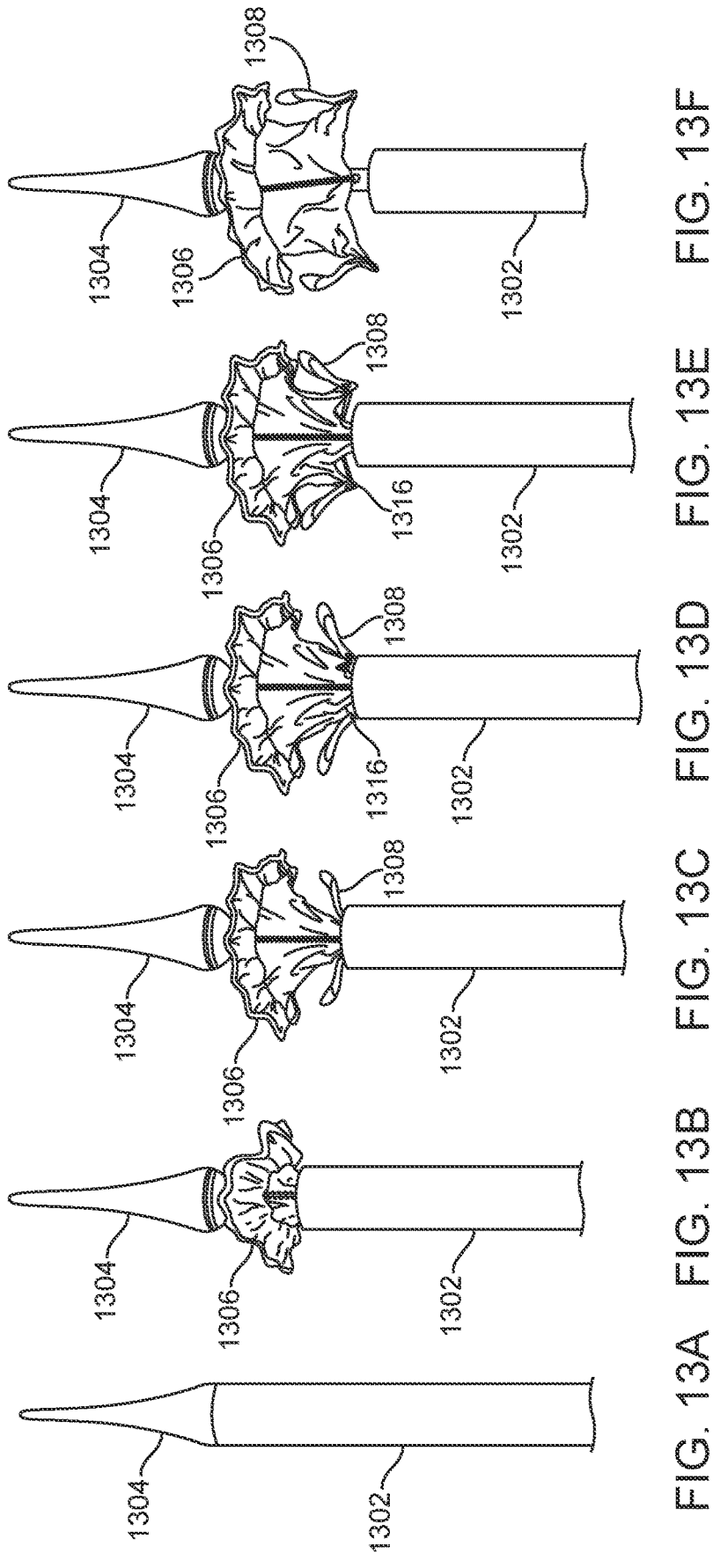
FIGS. 13A-13F show an example of deployment of a prosthesis using a tether control mechanism.

FIG. 13A shows a transapical delivery catheter having an outer sheath 1302 and a tapered distal tip 1304 that can be introduced through the chest wall and transapically into the heart.

In FIG. 13B the sheath 1302 is retracted proximally to expose the prosthesis, here a prosthetic mitral valve 1306 which allows the atrial portion to begin to self-expand. The atrial flange begins to form.

In FIG. 13C, further proximal retraction of sheath 1302 allows the atrial flange to fully expand, along with the annular portion and the ventricular anchor tabs 1308 partially self-expand into a horizontal or transverse position relative to the longitudinal axis of the prosthesis 1306. The elbows of the ventricular anchor tabs remain constrained by the sheath 1302 preventing them from expanding outward.

FIG. 13D shows that further proximal retraction of sheath 1302 releases the sheath from constraining the ventricular anchor tabs 1308 including the elbows and they may expand outward further but the elbows remain tethered 1310 using any of the tether mechanisms disclosed herein. In this example, the atrial flange self-expands without any control mechanism, but one of skill in the art will appreciate that any of the control mechanisms such as a lasso described herein may also be used to control the atrial end of the prosthesis. Thus, in this example, the atrial flange is fully expanded while the ventricular end is expanded but still constrained and not fully expanded. If repositioning or recapture is needed, tension in the ventricular tethers may be applied to re-collapse the device and allow repositioning.

Once the prosthesis is properly positioned, tension in the tethers is released allowing the ventricular anchors to fully expand as seen in FIG. 13E.

FIG. 13F shows release of the tethers from the ventricular anchors thereby decoupling the prosthesis from the delivery catheter. The ventricular anchors expand into a more vertical position that is substantially parallel with the longitudinal axis of the prosthesis. The catheter may then be removed from the patient leaving the prosthesis implanted into the native heart valve.

Prosthesis

FIGS. 14A-14D illustrate an example of a prosthetic mitral valve that may be deployed with any of the examples of delivery catheters, introducer sheaths, and/or steerable catheters described herein. One of skill in the art will appreciate that the prosthesis is not limited to a mitral valve prosthesis and the prosthesis may be any prosthesis including other prosthetic valves such as a prosthetic aortic valve, prosthetic pulmonary valve, prosthetic tricuspid valve, a prosthetic venous valve, or any other prosthetic. The prosthesis illustrated in FIGS. 14A-14D may be modified to accommodate any of the deployment control features described above. For example, the prosthesis may include apertures, hooks, or other connectors that allow the prosthesis to be coupled to a lasso or tether. FIGS. 14A-14D also illustrate the elbows that are referred to above.

Figure 14A:
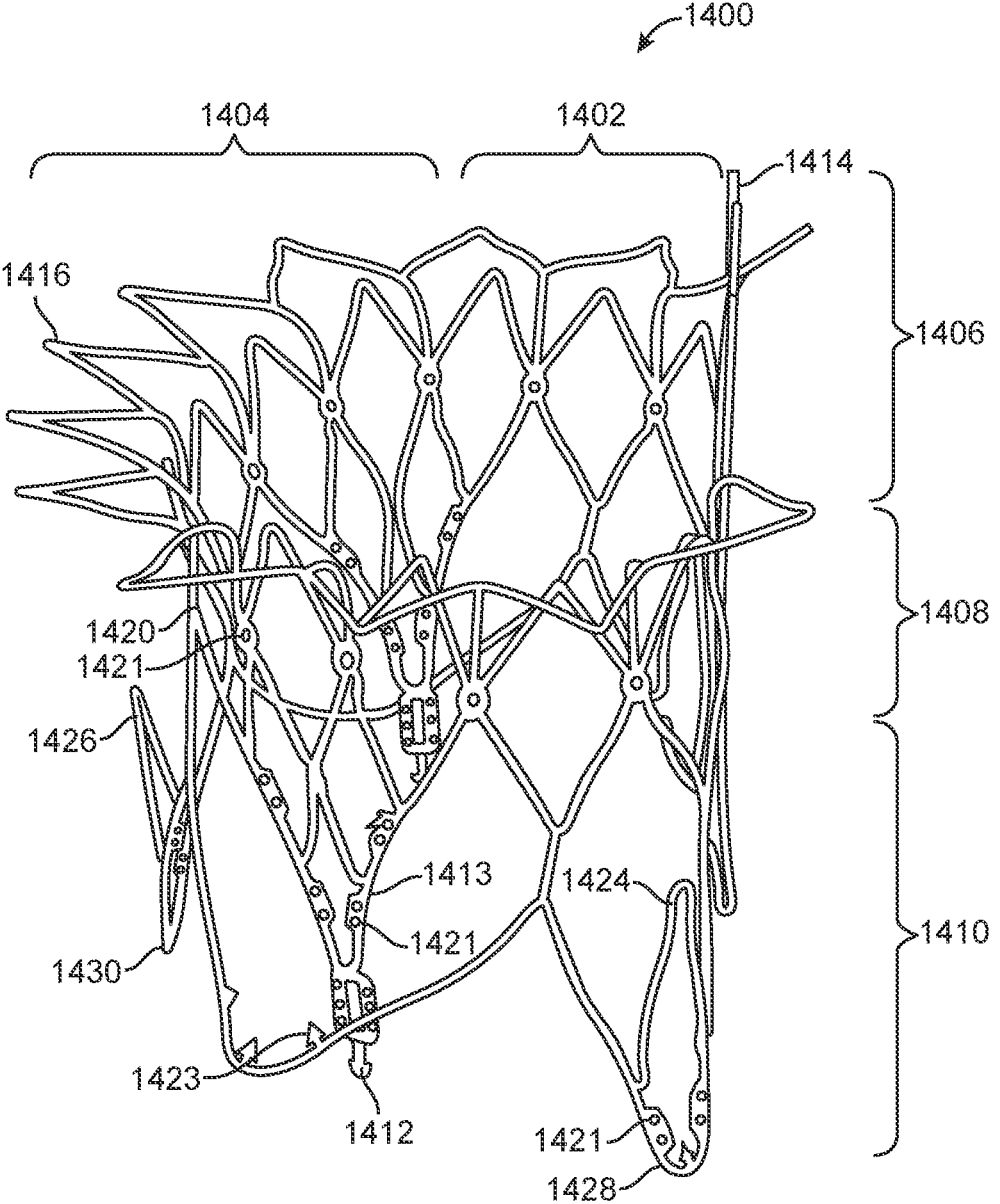
FIG. 14A is a perspective view of a prosthetic mitral valve.
Figure 14B:
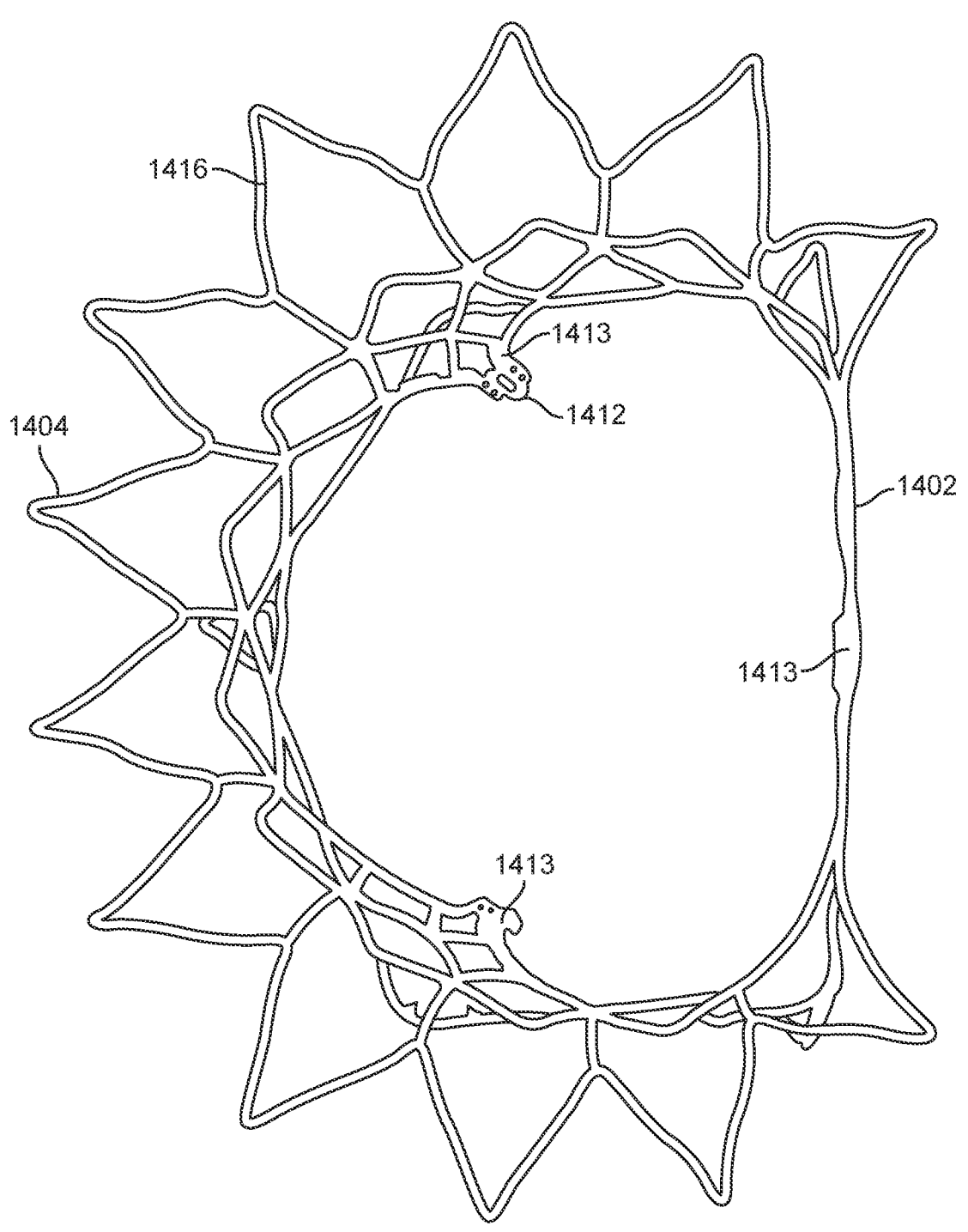
FIG. 14B is a top view of the prosthetic valve in FIG. 14A.

FIG. 14A illustrates a perspective view of an example of a prosthetic mitral valve with optional coverings removed to allow visibility of the anchor struts. FIG. 14B illustrates a top view of the prosthetic valve in FIG. 14A from the atrium looking down into the ventricle. The valve 1400 includes an asymmetrical expanded anchor portion having a D-shaped cross-section. As shown, the anchor portion generally comprises anterior 1402 and posterior 1404 aspects along the longitudinal axis thereof, as well as atrial 1406, annular 1408 and ventricular 1410 regions. Commissures (also referred to herein as commissure posts) 1413 are also shown. The prosthetic valve 1400 has a collapsed configuration and an expanded configuration. The collapsed configuration is adapted for loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other examples, the anchor may be expandable with an expandable member such as a balloon. In examples, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 1416 forms a flanged region that helps to anchor the prosthetic valve to the atrium, above the mitral valve. The atrial skirt includes a plurality of triangular fingers which extend radially outward from the anchor to form the flange. The posterior 1404 portion of the atrial skirt 1416 is generally round or circular, while a portion of the anterior 1402 part of the atrial skirt 1416 is flat. Thus, the atrial skirt region may have a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some examples, the atrial skirt lies in a plane that is substantially perpendicular to the central axis of the valve. The anterior portion 1402 of the atrial skirt 1406 optionally includes an alignment element 1414 which may be one or more struts which extend vertically upward and substantially parallel to the prosthetic valve. The alignment element 1414 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 1420 which also has a collapsed configuration for delivery, and an expanded configuration for anchoring the prosthetic valve along the native valve annulus. The annular region is also comprised of a plurality of interconnected struts that form a series of cells, that may be closed. Suture holes 1421 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in any example has a posterior portion 1404 which is circular, and an anterior portion 1402 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 1428 which also shows the ventricular anchor tab elbow. The ventricular skirt region also has a collapsed configuration for delivery, and an expanded configuration for anchoring. It is formed from a plurality of interconnected struts that form a series of cells, that may be closed, that can radially expand. The ventricular skirt in the expanded configuration anchors the prosthetic valve to the ventricle by expanding against the native mitral valve leaflets. Optional barbs 1423 in the ventricular skirt may be used to further help anchor the prosthetic valve into the ventricular tissue. Barbs may optionally also be included in the atrial skirt portion as well as the annular region of the anchor. Additionally, optional suture holes 1421 in the ventricular skirt may be used to help suture tissue or another material to the ventricular skirt region, similarly as discussed above. The anterior 1402 portion of the ventricular skirt may be flat, and the posterior 1404 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as has been discussed previously.

The ventricular skirt portion may optionally also include a pair of ventricular trigonal tabs 1424 on the anterior portion of the anchor (only 1 visible in this view) for helping to anchor the prosthetic valve as discussed in greater in this specification. The ventricular skirt may also optionally include a posterior tab 1426 on a posterior portion 1404 of the ventricular skirt for anchoring the prosthetic valve to a posterior portion of the annulus. The trigonal tabs 1424 or the posterior tab 1426 are tabs that extend radially outward from the anchor, and they are inclined upward in the upstream direction.

The actual valve mechanism is formed from three commissures posts (also referred to as commissures) 1413 which extend radially inward toward the central axis of the anchor in a funnel or cone-like shape. The commissures 1413 are formed from a plurality of interconnected struts that create the triangular shaped commissures. The struts of the commissures may include one or more suture holes 1421 that allow tissue or a synthetic material to be attached to the commissures. In this example, the valve is a tricuspid valve, therefore it includes three commissures 1413. The tips of the commissures may include a commissure tab 1412 (also referred to as a tab) for engaging a delivery catheter such as the slotted region in the hub or anchor element previously discussed above. In this example, the tabs have enlarged head regions connected to a narrower neck, forming a mushroom-like shape. The commissures may be biased in any position, but may angle inward slightly toward the central axis of the prosthetic valve so that retrograde blood flow forces the commissures into apposition with one another to close the valve, and antegrade blood flow pushes the commissures radially outward, to fully open the valve.

FIG. 14B is a top view illustrating the prosthetic valve of FIG. 14A from the atrial side, and shows the D-shaped cross-section.

Figure 14C:
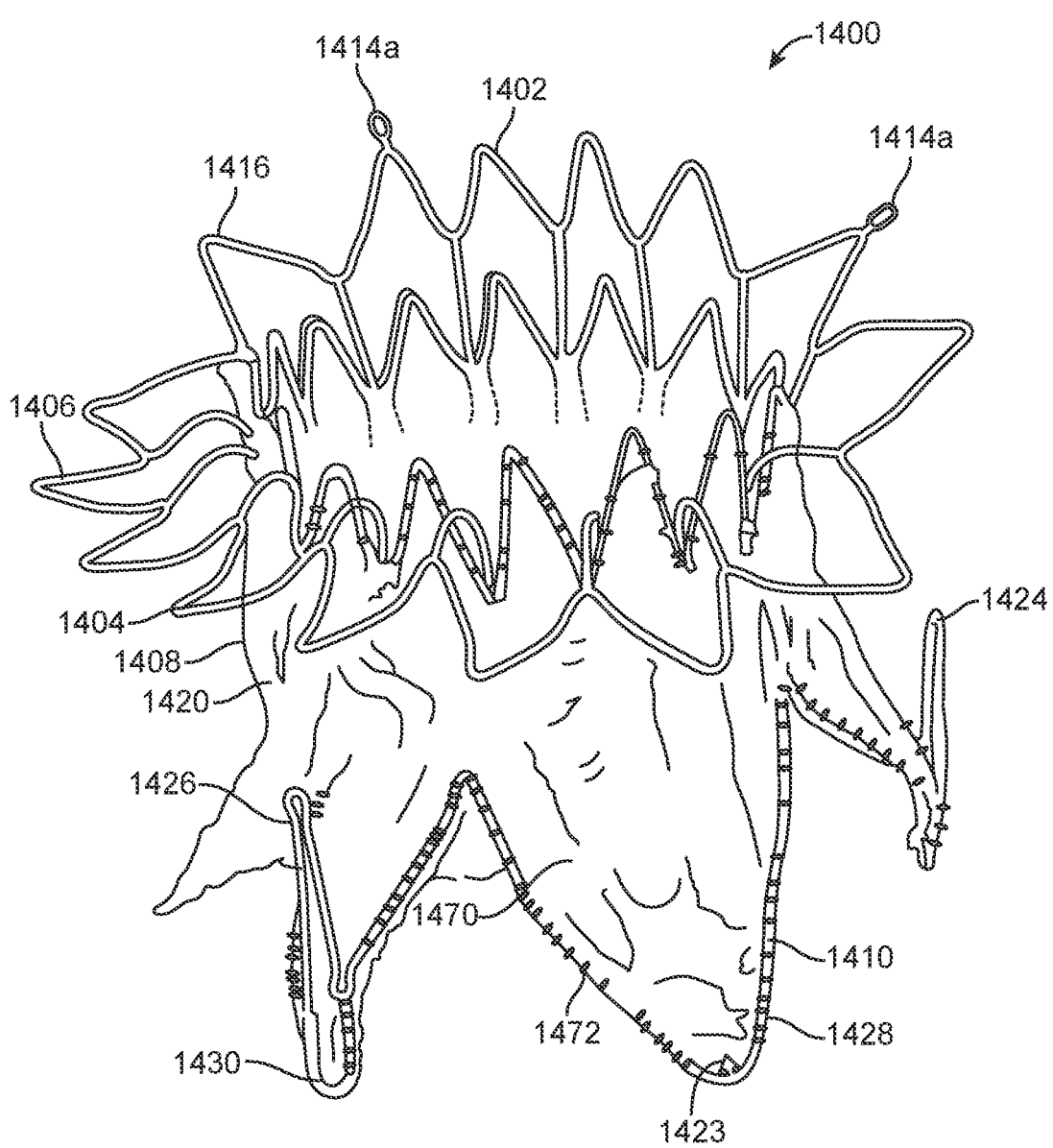
FIG. 14C illustrates a perspective view of the prosthetic valve in FIG. 14A.

FIG. 14C illustrates the prosthetic mitral valve of FIGS. 14A-14B with a covering 1470 coupled to portions of the anchor with suture 1472. This view is taken from an atrial perspective. In this example, the covering may be pericardium which may come from a number of sources such a bovine pericardium, porcine pericardium or other sources of pericardial tissue. In alternative examples, the covering may be a polymer such as Dacron polyester, ePTFE, or another synthetic material. The covering may be disposed over the annular region 1420 and the ventricular skirt region 1428, and in some examples the anterior ventricular trigonal 1424 tabs and the ventricular posterior tab 1430 may also be covered with the same or a different material. The covering helps seal the anchor against the adjacent tissue so that blood funnels through the valve mechanism. In this example, the atrial skirt is left uncovered, as well as tabs 1424, 1430. Additionally, radiopaque markers 1414 may form a portion of the alignment element and facilitate visualization of the prosthetic valve under fluoroscopy which may be important during alignment of the valve.

Figure 14D:
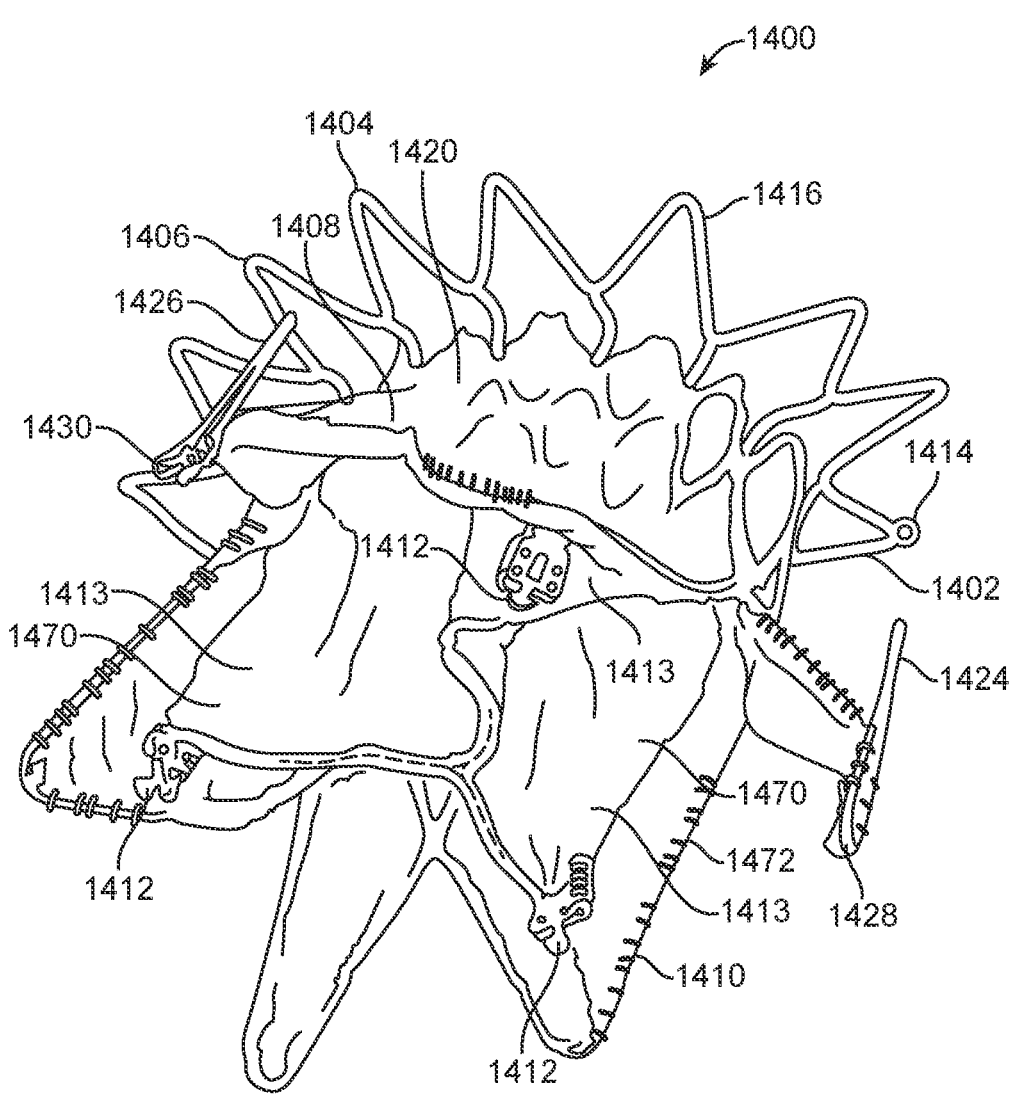
FIG. 14D illustrates a perspective view of the prosthetic valve in FIG. 14A.

FIG. 14D is a perspective view of the prosthetic mitral valve seen in FIG. 14C, as seen from the ventricle. The struts of the valve commissures are covered with the same material or a different material as the annular and ventricular regions as discussed above, thereby forming the tricuspid valve leaflets 1413. FIG. 14D shows the valve in the closed configuration where the three leaflets are engaged with one another preventing retrograde blood flow. Commissure tabs

1412 remain uncovered and allow the commissures to be coupled with a delivery device as will be explained below. The prosthetic valve in FIGS. 14C-14D may be sterilized so they are suitable for implantation in a patient using methods known in the art.

In any of the examples disclosed herein, one of skill in the art will appreciate that proximal and distal movement is relative and therefore proximal movement of one shaft relative to another shaft may be result of strictly proximal movement of one shaft relative to the other shaft, or the other shaft may be advanced distally relative to the one shaft, or a combination of proximal and distal movement of both shafts may result in proximal movement. A similar situation exists for distal movement of one shaft relative to another. Therefore, the relative motion may be created by any of these movements.

Notes and Examples

The following, non-limiting examples, detail certain aspects of the present subject matter to solve the challenges and provide the benefits discussed herein, among others.

Example 1 is a prosthesis delivery catheter, comprising: an inner distal capsule shaft having a proximal end, a distal end and a distal capsule coupled to the distal end thereof, wherein the distal capsule is configured to house the prosthesis; an anchor catheter having a proximal end and a distal end, the anchor catheter slidably disposed over the inner distal capsule shaft, wherein the anchor catheter further comprises an anchor hub coupled to a distal end of the anchor catheter, and wherein the anchor hub comprises a plurality of axially oriented slots configured to receive a strut of the prosthesis; an elbow catheter having a proximal end and a distal end, the elbow catheter slidably disposed over the anchor catheter; a peg plate assembly adjacent the anchor hub, the peg plate assembly comprising a plurality of protruding pegs and a plate, the peg plate assembly having an open configuration and a closed configuration, wherein in the closed configuration the plurality of pegs abut the plate to hold one or more tethers around the plurality of protruding pegs, and the in open configuration the plurality of pegs are disposed away from the plate to leave a gap therebetween to allow release of the one or more tethers from the plurality of pegs.

Example 2 is the catheter of Example 1, wherein the one or more tethers are configured to be coupled to an elbow of an anchor tab on the prosthesis, and wherein the one or more tethers control radial expansion and contraction of the elbow.

Example 3 is the catheter of any of Examples 1-2, wherein the one or more tethers are configured to hold the elbow of the anchor tab in a radially collapsed configuration while under tension, and wherein the one or more tethers are configured to allow radial expansion of the elbow when tension is relaxed.

Example 4 is the catheter of any of Examples 1-3, wherein the one or more tethers are coupled to the elbow catheter, and wherein axial movement of the elbow catheter in a first direction applies tension to the one or more tethers, and wherein axial movement of the elbow catheter in a second direction opposite the first direction relieves tension from the one or more tethers.

Example 5 is the catheter of any of Examples 1-4, wherein the one or more tethers are coupled to an actuator disposed on a proximal end of the delivery catheter, and wherein actuation of the actuator in a first direction applies tension to the one or more tethers, and wherein actuation of the actuator in a second direction opposite the first direction relieves tension from the one or more tethers.

Example 6 is the catheter of any of Examples 1-5, wherein the peg plate assembly further comprises a resilient spring element having an expanded configuration and a collapsed configuration, wherein in the expanded configuration the resilient spring element holds the peg plate assembly in the closed configuration, and wherein the resilient spring in the collapsed configuration allows the peg plate assembly to move into the open configuration.

Example 7 is the catheter of any of Examples 1-6, further comprising an inner lasso catheter slidably disposed over the elbow catheter, and an outer lasso catheter slidably disposed over the inner lasso catheter, wherein one of the inner or outer lasso catheters comprises a protruding peg adjacent a distal end of the respective inner or outer lasso catheter, and the other of the inner or outer lasso catheter comprises a slot for receiving the protruding peg, the slot disposed adjacent a distal end of the other of the inner or outer lasso catheter, wherein actuation of the inner lasso catheter relative to the outer lasso catheter opens or closes a gap between the protruding peg and the slot to either hold or release a lasso.

Example 8 is the catheter of any of Examples 1-7, wherein the lasso is coupled to an atrial portion of the prosthesis, and wherein application of tension to the lasso holds the atrial portion of the prosthesis in a collapsed configuration, and wherein the atrial portion expands upon release of the tension in the lasso.

Example 9 is the catheter of any of Examples 1-8, wherein the prosthesis comprises an atrial flange and the lasso is circumferentially disposed around the atrial flange, and wherein the lasso further comprises a second circumferential loop around a downstream portion of the prosthesis.

Example 10 is the catheter of any of Examples 1-9, wherein the lasso is coupled to an actuator disposed on a proximal end of the delivery catheter, and wherein actuation of the actuator in a first direction applies tension to the lasso, and wherein actuation of the actuator in a second direction opposite the first direction relieves tension from the lasso.

Example 11 is the catheter of any of Examples 1-10, wherein one or more of the inner distal capsule shaft, the anchor catheter and the elbow catheter comprises a flexible region adjacent a distal end of the delivery catheter, wherein the flexible region comprises a plurality of slots oriented transversely to a longitudinal axis of the delivery catheter.

Example 12 is a delivery system for delivering a prosthesis to a target treatment region, the system comprising: the delivery catheter of any of Examples 1-11, and the prosthesis carried by the delivery catheter.

Example 13 is the delivery system of Example 12, wherein the prosthesis is a prosthetic mitral valve.

Example 14 is the delivery system of any of Examples 12-13, further comprising an introducer sheath configured to be slidably disposed over the delivery catheter.

Example 15 is the delivery system of any of Examples 12-14, wherein the introducer sheath is a steerable introducer sheath.

Example 16 is the delivery system of any of Examples 12-15, further comprising a steering catheter configured to be slidably disposed over the delivery catheter, and wherein steering of the steering catheter steers a distal end of the delivery catheter.

Example 17 is a method for delivering a prosthetic heart valve to a native heart valve in a patient, the method comprising: advancing a delivery catheter carrying the prosthetic heart valve to the native heart valve; radially expanding a superior portion of the prosthetic heart valve to engage a superior portion of the native heart valve; radially expanding an inferior portion of the prosthetic heart valve to engage an inferior portion of the native heart valve; detaching the prosthetic heart valve from the delivery catheter; and removing the delivery catheter from the patient.

Example 18 is the method of Example 17, wherein advancing the delivery catheter comprises transapically delivering the prosthetic heart valve to the native heart valve.

Example 19 is the method of any of Examples 17-18, wherein advancing the delivery catheter comprises transseptally delivering the prosthetic heart valve to the native heart valve.

Example 20 is the method of any of Examples 17-19, wherein radially expanding the superior portion of the prosthetic valve comprises radially expanding an atrial flange into engagement with an atrial floor of the native heart valve.

Example 21 is the method of any of Examples 17-20, wherein radially expanding the superior portion of the prosthetic valve comprises releasing a lasso from constraining the superior portion.

Example 22 is the method of any of Examples 17-21, wherein releasing the lasso comprises slidably moving an elongate shaft coupled to the lasso to release tension in the lasso so that the superior portion expands.

Example 23 is the method of any of Examples 17-22, wherein releasing the lasso comprises slidably moving an inner lasso shaft relative to an outer lasso shaft to open a gap between a protruding peg on one of the inner lasso catheter or outer lasso catheter and a slot on the other of the inner lasso catheter and the outer lasso catheter, thereby releasing the lasso from the delivery catheter.

Example 24 is the method of any of Examples 17-23, wherein radially expanding the inferior portion comprises radially expanding one or more anchor tabs into engagement with subannular tissue in a ventricle of the native heart valve.

Example 25 is the method of any of Examples 17-24, wherein radially expanding the inferior portion comprises releasing a tether from constraining an anchor tab on the prosthetic heart valve.

Example 26 is the method of any of Examples 17-25, wherein releasing the tether comprises slidably moving an elongate shaft coupled to the tether to release tension in the tether so that the anchor tab expands.

Example 27 is the method of any of Examples 17-26, wherein releasing the tether comprises slidably moving an anchor catheter relative to an elbow catheter to open a gap between a protruding peg on one of the anchor catheter or the elbow catheter and a plate on the other of the anchor catheter and elbow catheter, thereby releasing the tether from the delivery catheter.

Example 28 is the method of any of Examples 17-27, wherein radially expanding the superior or inferior portions of the prosthetic heart valve comprise removing the prosthetic heart valve from a distal capsule disposed on a distal end of an elongate inner capsule shaft on the delivery catheter.

Example 29 is the method of any of Examples 17-28, wherein detaching the prosthetic heart valve comprises releasing one or more struts on the prosthetic heart valve from slots disposed in an anchor hub coupled to a distal end of an anchor catheter on the delivery catheter.

Example 30 is the method of any of Examples 17-29, wherein the native heart valve is a native mitral valve and the prosthetic heart valve is a prosthetic mitral valve.

Example 31 is the method of any of Examples 17-30, further comprising steering the delivery catheter by steering an introducer sheath disposed thereover, or by steering a steering catheter disposed thereover.

Example 32 is the method of any of Examples 17-31, further comprising retrieving the prosthetic heart valve by radially collapsing the superior portion of the prosthetic heart valve.

Example 33 is the method of any of Examples 17-32, further comprising retrieving the prosthetic heart valve by radially collapsing the inferior portion of the prosthetic heart valve.

In Example 34, the apparatuses or methods of any one or any combination of Examples 1-33 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A prosthesis delivery catheter, comprising:

an inner distal capsule shaft having a proximal end, a distal end and a distal capsule coupled to the distal end thereof, wherein the distal capsule is configured to house the prosthesis;

an anchor catheter having a proximal end and a distal end, the anchor catheter slidably disposed over the inner distal capsule shaft, wherein the anchor catheter further comprises an anchor hub coupled to a distal end of the anchor catheter, and wherein the anchor hub comprises a plurality of axially oriented slots configured to receive a strut of the prosthesis;

an elbow catheter having a proximal end and a distal end, the elbow catheter slidably disposed over the anchor catheter;

a peg plate assembly adjacent the anchor hub, the peg plate assembly comprising a plurality of protruding pegs and a plate, the peg plate assembly having an open configuration and a closed configuration, wherein in the closed configuration the plurality of pegs abut the plate to hold one or more tethers around the plurality of protruding pegs, and the in open configuration the plurality of pegs are disposed away from the plate to leave a gap therebetween to allow release of the one or more tethers from the plurality of pegs.

2. The catheter of claim 1, wherein the one or more tethers are configured to be coupled to an elbow of an anchor tab on the prosthesis, and wherein the one or more tethers control radial expansion and contraction of the elbow.

3. The catheter of claim 2, wherein the one or more tethers are configured to hold the elbow of the anchor tab in a radially collapsed configuration while under tension, and wherein the one or more tethers are configured to allow radial expansion of the elbow when tension is relaxed.

4. The catheter of claim 3, wherein the one or more tethers are coupled to the elbow catheter, and wherein axial movement of the elbow catheter in a first direction applies tension to the one or more tethers, and wherein axial movement of the elbow catheter in a second direction opposite the first direction relieves tension from the one or more tethers.

5. The catheter of claim 3, wherein the one or more tethers are coupled to an actuator disposed on a proximal end of the delivery catheter, and wherein actuation of the actuator in a first direction applies tension to the one or more tethers, and wherein actuation of the actuator in a second direction opposite the first direction relieves tension from the one or more tethers.

6. The catheter of claim 1, wherein the peg plate assembly further comprises a resilient spring element having an expanded configuration and a collapsed configuration, wherein in the expanded configuration the resilient spring element holds the peg plate assembly in the closed configuration, and wherein the resilient spring in the collapsed configuration allows the peg plate assembly to move into the open configuration.

7. The catheter of claim 1, further comprising an inner lasso catheter slidably disposed over the elbow catheter, and an outer lasso catheter slidably disposed over the inner lasso catheter, wherein one of the inner or outer lasso catheters comprises a protruding peg adjacent a distal end of the respective inner or outer lasso catheter, and the other of the inner or outer lasso catheter comprises a slot for receiving the protruding peg, the slot disposed adjacent a distal end of the other of the inner or outer lasso catheter, wherein actuation of the inner lasso catheter relative to the outer lasso catheter opens or closes a gap between the protruding peg and the slot to either hold or release a lasso.

8. The catheter of claim 7, wherein the lasso is coupled to an atrial portion of the prosthesis, and wherein application of tension to the lasso holds the atrial portion of the prosthesis in a collapsed configuration, and wherein the atrial portion expands upon release of the tension in the lasso.

9. The catheter of claim 8, wherein the prosthesis comprises an atrial flange and the lasso is circumferentially disposed around the atrial flange, and wherein the lasso further comprises a second circumferential loop around a downstream portion of the prosthesis.

10. The catheter of claim 8, wherein the lasso is coupled to an actuator disposed on a proximal end of the delivery catheter, and wherein actuation of the actuator in a first direction applies tension to the lasso, and wherein actuation of the actuator in a second direction opposite the first direction relieves tension from the lasso.

11. The catheter of claim 1, wherein one or more of the inner distal capsule shaft, the anchor catheter and the elbow catheter comprises a flexible region adjacent a distal end of the delivery catheter, wherein the flexible region comprises a plurality of slots oriented transversely to a longitudinal axis of the delivery catheter.

12. A delivery system for delivering a prosthesis to a target treatment region, the system comprising:

the delivery catheter of claim 1, and the prosthesis carried by the delivery catheter.

13. The delivery system of claim 12, wherein the prosthesis is a prosthetic mitral valve.

14. The delivery system of claim 12, further comprising an introducer sheath configured to be slidably disposed over the delivery catheter.

15. The delivery system of claim 14, wherein the introducer sheath is a steerable introducer sheath.

16. The delivery system of claim 12, further comprising a steering catheter configured to be slidably disposed over the delivery catheter, and wherein steering of the steering catheter steers a distal end of the delivery catheter.

17. A method for delivering a prosthetic heart valve to a native heart valve in a patient, the method comprising:

advancing a delivery catheter carrying the prosthetic heart valve to the native heart valve;

radially expanding a superior portion of the prosthetic heart valve to engage a superior portion of the native heart valve, wherein radially expanding the superior portion of the prosthetic valve comprises releasing a lasso from constraining the superior portion, and wherein releasing the lasso comprises slidably moving an inner lasso shaft relative to an outer lasso shaft to open a gap between a protruding peg on one of the inner lasso catheter or outer lasso catheter and a slot on the other of the inner lasso catheter and the outer lasso catheter, thereby releasing the lasso from the delivery catheter;

radially expanding an inferior portion of the prosthetic heart valve to engage an inferior portion of the native heart valve;

detaching the prosthetic heart valve from the delivery catheter; and removing the delivery catheter from the patient.

18. The method of claim 17, wherein advancing the delivery catheter comprises transapically delivering the prosthetic heart valve to the native heart valve.

19. The method of claim 17, wherein advancing the delivery catheter comprises transseptally delivering the prosthetic heart valve to the native heart valve.

20. The method of claim 17, wherein radially expanding the superior portion of the prosthetic valve comprises radially expanding an atrial flange into engagement with an atrial floor of the native heart valve.

21. The method of claim 17, wherein releasing the lasso comprises slidably moving an elongate shaft coupled to the lasso to release tension in the lasso so that the superior portion expands.

22. The method of claim 17, wherein radially expanding the inferior portion comprises radially expanding one or more anchor tabs into engagement with subannular tissue in a ventricle of the native heart valve.

23. The method of claim 17, wherein radially expanding the inferior portion comprises releasing a tether from constraining an anchor tab on the prosthetic heart valve.

24. The method of claim 23, wherein releasing the tether comprises slidably moving an elongate shaft coupled to the tether to release tension in the tether so that the anchor tab expands.

25. The method of claim 23, wherein releasing the tether comprises slidably moving an anchor catheter relative to an elbow catheter to open a gap between a protruding peg on one of the anchor catheter or the elbow catheter and a plate on the other of the anchor catheter and elbow catheter, thereby releasing the tether from the delivery catheter.

26. The method of claim 17, wherein radially expanding the superior or inferior portions of the prosthetic heart valve comprise removing the prosthetic heart valve from a distal capsule disposed on a distal end of an elongate inner capsule shaft on the delivery catheter.

27. The method of claim 17, wherein detaching the prosthetic heart valve comprises releasing one or more struts on the prosthetic heart valve from slots disposed in an anchor hub coupled to a distal end of an anchor catheter on the delivery catheter.

28. The method of claim 17, wherein the native heart valve is a native mitral valve and the prosthetic heart valve is a prosthetic mitral valve.

29. The method of claim 17, further comprising steering the delivery catheter by steering an introducer sheath disposed thereover, or by steering a steering catheter disposed thereover.

30. The method of claim 17, further comprising retrieving the prosthetic heart valve by radially collapsing the superior portion of the prosthetic heart valve.

31. The method of claim 17, further comprising retrieving the prosthetic heart valve by radially collapsing the inferior portion of the prosthetic heart valve.

32. A method for delivering a prosthetic heart valve to a native heart valve in a patient, the method comprising:

advancing a delivery catheter carrying the prosthetic heart valve to the native heart valve;

radially expanding a superior portion of the prosthetic heart valve to engage a superior portion of the native heart valve;

radially expanding an inferior portion of the prosthetic heart valve to engage an inferior portion of the native heart valve, wherein radially expanding the inferior portion comprises releasing a tether from constraining an anchor tab on the prosthetic heart valve, and wherein releasing the tether comprises slidably moving an anchor catheter relative to an elbow catheter to open a gap between a protruding peg on one of the anchor catheter or the elbow catheter and a plate on the other of the anchor catheter and elbow catheter, thereby releasing the tether from the delivery catheter;

detaching the prosthetic heart valve from the delivery catheter; and removing the delivery catheter from the patient.

33. The method of claim 32, wherein advancing the delivery catheter comprises transapically delivering the prosthetic heart valve to the native heart valve.

34. The method of claim 32, wherein advancing the delivery catheter comprises transseptally delivering the prosthetic heart valve to the native heart valve.

35. The method of claim 32, wherein radially expanding the superior portion of the prosthetic valve comprises radially expanding an atrial flange into engagement with an atrial floor of the native heart valve.

36. The method of claim 32, wherein radially expanding the superior portion of the prosthetic valve comprises releasing a lasso from constraining the superior portion.

37. The method of claim 36, wherein releasing the lasso comprises slidably moving an elongate shaft coupled to the lasso to release tension in the lasso so that the superior portion expands.

38. The method of claim 32, wherein radially expanding the inferior portion comprises radially expanding one or more anchor tabs into engagement with subannular tissue in a ventricle of the native heart valve.

39. The method of claim 32, wherein releasing the tether comprises slidably moving an elongate shaft coupled to the tether to release tension in the tether so that the anchor tab expands.

40. The method of claim 32, wherein radially expanding the superior or inferior portions of the prosthetic heart valve comprise removing the prosthetic heart valve from a distal capsule disposed on a distal end of an elongate inner capsule shaft on the delivery catheter.

41. The method of claim 32, wherein detaching the prosthetic heart valve comprises releasing one or more struts on the prosthetic heart valve from slots disposed in an anchor hub coupled to a distal end of an anchor catheter on the delivery catheter.

42. The method of claim 32, wherein the native heart valve is a native mitral valve and the prosthetic heart valve is a prosthetic mitral valve.

43. The method of claim 32, further comprising steering the delivery catheter by steering an introducer sheath disposed thereover, or by steering a steering catheter disposed thereover.

44. The method of claim 32, further comprising retrieving the prosthetic heart valve by radially collapsing the superior portion of the prosthetic heart valve.

45. The method of claim 32, further comprising retrieving the prosthetic heart valve by radially collapsing the inferior portion of the prosthetic heart valve.

* * * * *